US008084210B2

(12) United States Patent
Gladding et al.

(10) Patent No.: US 8,084,210 B2
(45) Date of Patent: *Dec. 27, 2011

(54) METHODS FOR THE ASSESSMENT OF DRUG RESPONSE

(75) Inventors: Patrick A. Gladding, Cleveland, OH (US); Arzu Gunes, Uppsala (SE); Marja-Liisa Dahl, Etero (SE); Mark W. Webster, Auckland (NZ)

(73) Assignee: Theranostics Laboratory, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 12/950,617

(22) Filed: Nov. 19, 2010

(65) Prior Publication Data

US 2011/0060532 A1 Mar. 10, 2011

Related U.S. Application Data

(63) Continuation of application No. 12/864,581, filed as application No. PCT/NZ2009/000008 on Jan. 23, 2009.

(60) Provisional application No. 61/023,596, filed on Jan. 25, 2008.

(51) Int. Cl.
| | |
|---|---|
| C12Q 1/68 | (2006.01) |
| G01N 33/48 | (2006.01) |
| A61K 31/44 | (2006.01) |
| C07H 21/04 | (2006.01) |
| C07D 513/02 | (2006.01) |

(52) U.S. Cl. ........ 435/6.11; 435/6.18; 702/19; 514/301; 536/23.2; 536/23.5; 546/114

(58) Field of Classification Search ......................... None
See application file for complete search history.

(56) References Cited

U.S. PATENT DOCUMENTS

| | | | |
|---|---|---|---|
| 5,478,723 A | 12/1995 | Parkinson et al. | |
| 5,912,120 A | 6/1999 | Goldstein et al. | |
| 5,989,844 A | 11/1999 | Shimada et al. | |
| 6,812,339 B1 | 11/2004 | Venter et al. | |
| 6,884,810 B2 | 4/2005 | Nagasawa et al. | |
| 6,986,992 B2 | 1/2006 | Chui et al. | |
| 7,833,744 B2 * | 11/2010 | Flockhart et al. | 435/25 |
| 2003/0059774 A1 | 3/2003 | Risinger et al. | |
| 2003/0103901 A1 | 6/2003 | Leyland-Jones | |
| 2004/0084867 A1 | 5/2004 | Leyland-Jones | |

(Continued)

FOREIGN PATENT DOCUMENTS

EP 0897015 5/2000

(Continued)

OTHER PUBLICATIONS

Sibbing, D. et al. Circulation 121:512-518 (Feb. 2010; published online Jan. 18, 2010).*

(Continued)

*Primary Examiner* — Diana Johannsen
(74) *Attorney, Agent, or Firm* — Casimir Jones, S.C.

(57) ABSTRACT

The present invention provides methods for predicting or determining a subject's response to an antiplatelet agent, and methods for determining a subject's suitability to a treatment regime or intervention for a disease associated with platelet aggregation, using analysis of genetic polymorphisms. The present invention also relates to the use of genetic polymorphisms in assessing a subject's response to an antiplatelet agent. Nucleotide probes and primers, kits, and microarrays suitable for such assessment are also provided.

3 Claims, 9 Drawing Sheets

U.S. PATENT DOCUMENTS

| | | | |
|---|---|---|---|
| 2004/0199333 | A1 | 10/2004 | Hoffman et al. |
| 2005/0191731 | A1* | 9/2005 | Judson et al. .................. 435/104 |
| 2006/0040295 | A1 | 2/2006 | Kumar et al. |
| 2006/0110767 | A1 | 5/2006 | Schuetz et al. |
| 2006/0259251 | A1 | 11/2006 | Warrington |
| 2008/0085240 | A1 | 4/2008 | Flockhart et al. |
| 2008/0248466 | A1 | 10/2008 | Gordon et al. |
| 2009/0087856 | A1 | 4/2009 | Caldwell et al. |
| 2009/0099030 | A1 | 4/2009 | Merante |
| 2009/0138286 | A1 | 5/2009 | Linder et al. |
| 2009/0233288 | A1 | 9/2009 | Hirai et al. |
| 2009/0269756 | A1 | 10/2009 | Majima et al. |

FOREIGN PATENT DOCUMENTS

| | | |
|---|---|---|
| WO | 02/38589 | 5/2002 |
| WO | 2002046209 | 6/2002 |
| WO | 2005038049 | 4/2005 |
| WO | 2007097884 | 8/2007 |
| WO | 2008066162 | 6/2008 |

OTHER PUBLICATIONS

Trenk, D. et al. Circulation 118(18):Suppl 2:S814-S815 (Oct. 2008).*

Dahlman, I et al. Nature Genetics 30:149-150 (Feb. 2002).*

Abell & Liu. "Abstract 272: In vitro Platelet Aggregation as a Biosensor for Clopidogrel Active Metabolite Formation," Circulation. 2006;114:II_27.

Brandt et al., "Common polymorphisms of CYP2C19 and CYP2C9 affect the pharmacokinetic and pharmacodynamic response to clopidogrel but not prasugrel," Journal of Thrombosis and Haemostasis (2007) vol. 5, Issue 12, pp. 2429-2436.

Brockimöller & Tzvetkov, "Pharmacogenetics: data, concepts and tools to improve drug discovery and drug treatment," Eur J Clin Pharmacol. Feb. 2008;64(2):133-57. Epub Jan. 26, 2008.

Chen et al., "Inhibition of ADP-Induced Platelet Aggregation by Clopidorgrel is Related to CYP2C19 Genetic Polymorphisms," Clin. and Exp. Pharma. and Physiol., 2008, 35:904-908.

Daniel & Edeki. "Genetic polymorphism of S-mephenytoin 4'-hydroxylation." Psychopharmacol Bull. 1996;32 (2):219-30.

Evans & Johnson, Annual Review of Genomics and Human Genetics 2 (2001), 9-39.

Farid et al., "Cytochrome P450 3A inhibition by ketoconazole affects prasugrel and clopidogrel pharmacokinetics and pharmacodynamics differently." Clin Pharm Ther., 2007, 81:735-741.

Fontana et al., "Biological effect of increased maintenance dose of clopidogrel in cardiovascular outpatients and influence of the cytochrome P450 2C19*2 allele on clopidogrel responsiveness," Thromb Res. 2008;121(4):463-8. Epub Aug. 2, 2007.

Fontana et al., "Influence of CYP2C19 and CYP3A4 gene polymorphisms on clopidogrel responsiveness in healthy subjects," J Thromb Haemost. Oct. 2007;5(10):2153-5. Epub Aug. 3, 2007.

Geisler et al. "CYP2C19 and nongenetic factors predict poor responsiveness to clopidogrel loading dose after coronary stent implantation." Pharmacogenomics. Sep. 2008;9(9):1251-9.

Goldstein & Blaisdell. "Genetic tests which identify the principal defects in CYP2C19 responsible for the polymorphism in mephenytoin metabolism." Methods Enzymol. 1996;272:210-8.

Hahnenberger, et al., "Use of oligonucleotide array hybridization for genotyping CYP2D6 and CYP2C19," 1997, Clinical Pharmacology and Therapeutics, 61(2):165.

Hulot et al., "Cytochrome P450 2C19 loss-of-function polymorphism is a major determinant of clopidogrel responsiveness in healthy subjects," Blood 108:2244-2247, Oct. 2006.

Ingelman-Sundberg et al., "Human drug metabolising cytochrome P450 enzymes: properties and polymorphisms," Naunyn Schmiedebergs Arch Pharmacol. Jan. 2004;369(1):89-104. Epub Oct. 22, 2003.

Ingelman-Sundberg et al., "Influence of cytochrome P450 polymorphisms on drug therapies: pharmacogenetic, pharmacoepigenetic and clinical aspects," Pharmacol Ther. Dec. 2007;116(3):496-526. Epub Oct. 9, 2007.

Ingelman-Sundberg et al., "Polymorphic human cytochrome P450 enzymes: an opportunity for individualized drug treatment," Trends Pharmacol Sci. Aug. 1999;20(8):342-9.

Kurzawski et al., "Effect of CYP2C19*17 gene variant on Helicobacter pylori eradication in peptic ulcer patients." Eur J Clin Pharmacol. Oct. 2006;62(10):877-80. Epub Aug. 16, 2006.

Payne et al. "Increased Active Metabolite Formation Explains the Greater Platelet Inhibition With Prasugrel Compared to High-dose Clopidogrel," Journal of Cardiovascular Pharmacology:Nov. 2007—vol. 50—Issue 5—pp. 555-562.

Rudberg et al., "Impact of the ultrarapid CYP2C19*17 allele on serum concentration of escitalopram in psychiatric patients," Clin Pharmacol Ther. Feb. 2008;83(2):322-7. Epub Jul. 11, 2007.

Sim et al., "A common novel CYP2C19 gene variant causes ultrarapid drug metabolism relevant for the drug response to proton pump inhibitors and antidepressants," 2006, Clinical Pharmacology & Therapeutics (2006) 79, 103-113.

Demorais et al., "Identification of a New Genetic Defect Responsible for the Polymorphism of (s)-Mephenytoin Metabolism in Japanese," Molecular Pharmacology, 1994, 46:594-598.

Desta et al., "Rapid Identification of Hepatic Cytochrome P450 2C19 Activity Using a Novel and Noninvasive [13C] Pantoprazole Breath Test," J Pharmacol. Exp. Thera., 2009, 329:297-305.

Freedman et al., "Clopidogrel, Genetics, and Drug Responsiveness," N Eng. J. Med., 2009, 360:411-413.

Helsby, N. A., "Pheno- or Genotype for the CYP2C19 Drug Metabolism Polymorphism: the Influence of Disease," Proc. West. Pharmacol. Soc., 2008, 51:5-10.

Mega et al., "Cytochrome P-450 Polymorphisms and Response to Clopidogrel," N Eng J Med., 2009, 360:354-362.

Simon et al., "Genetic Determinants of Response to Clopidogrel and Cardiovascular Events," N Eng J Med., 2009, 360:363-375.

* cited by examiner

US 8,084,210 B2

METHODS FOR THE ASSESSMENT OF DRUG RESPONSE

CROSS-REFERENCE INFORMATION

The present application is a continuation of pending U.S. patent application Ser. No. 12/864,581, filed Nov. 3, 2010, which is a U.S. National Entry of International Patent Application of PCT/NZ2009/000008, filed Jan. 23, 2009, which claims the benefit of U.S. Provisional Patent Application 61/023,596, filed Jan. 25, 2008.

FIELD OF THE INVENTION

Fields of the invention include responses to pharmaceutical drugs, methods for assessment of drug responses and prediction of subject responses to particular drugs and drug treatment regimes, and analyses of genetic polymorphisms and altered gene expression.

BACKGROUND OF THE INVENTION

The following includes information that may be useful in understanding the present inventions. It is not an admission that any of the information provided herein is prior art, or relevant, to the presently described or claimed inventions, or that any publication or document that is specifically or implicitly referenced is prior art.

One recent technological focus in the field of human genomics is pharmacogenomics, which includes efforts to use human DNA sequence variability in the development and prescription of drugs. Pharmacogenomics is based on the correlation or association between a given genotype and a resulting phenotype. Since the first correlation study over half-a-century ago linking adverse drug response with amino acid variations in two drug-metabolizing enzymes (plasma cholinesterase and glucose-6-phosphate dehydrogenase), various studies have reported on sequence polymorphisms within drug metabolism enzymes, drug targets and drug transporters and correlations with compromised levels of drug efficacy or safety.

Pharmacogenomics information will be especially useful in clinical settings where correlation information can be used to prevent drug toxicities, or develop treatment regimes. For example, patients are often screened for genetic differences in the thiopurine methyltransferase gene that cause decreased metabolism of 6-mercaptopurine or azathioprine. However, only a small percentage of observed drug toxicities have been explained adequately by the set of pharmacogenomic markers available to date.

In addition, "outlier" individuals, or individuals experiencing unanticipated effects in clinical trials (when administered drugs that have previously been demonstrated to be both safe and efficacious), can cause substantial delays in obtaining FDA drug approval and may even cause certain drugs to come off market, though such drugs may be efficacious for a majority of recipients.

Biotechnological methods used to date to identify target genomic regions include, for example, differential gene expression (which essentially looks for differences in gene expression between control and case samples); protein-protein interaction maps which are used to identify drug receptors and their immediate effectors; and mining human sequence databases for sequences similar to known disease-related, pharmacokinetic or pharmacodynamic regulators. In comparison, association studies that correlate and validate genomic regions with a particular phenotypic trait rely on population genetics and robust statistical metrics. Association studies provide a powerful tool to obtain greater amounts of information in a shorter amount of time thus reducing costs of research and development efforts.

Because all humans are 99.9% identical in their genetic makeup, the DNA sequence of any two individuals is nearly identical. Variations between individuals include, for example, deletions or insertions of DNA sequences, variations in the number of repetitive DNA elements in non-coding regions and changes in a single nucleotide position, or "single nucleotide polymorphisms" (SNP).

SNPs are useful for conducting association studies, and have been identified as potentially useful genetic markers for phenotypic traits. Phenotypic traits of particular interest to the medical field include predisposition to disease, and response to a particular drug or treatment regime.

For example, recent studies report that the response to the antiplatelet agent clopidogrel is variable, with 20-40% of patients being classified as poor responders or resistant to clopidogrel due to low inhibition of ADP-induced platelet aggregation or activation (Angiolillo D J et al. (2005); Gurbel P A et al. (2003); Gurbel P A et al. (2006); Gurbel P A, Bliden, K P, Hayes K M et al. (2005); Mobley, J E et al. (2004); and Muller I et al. (2003)). Metabolising enzymes (e.g. cytochrome CYP450 system) and gut absorptive mechanisms (e.g. p-glycoprotein efflux pump) may be responsible for this variability. The activity of CYP3A4, measured by radiolabelled erythromycin breath testing, has reportedly been correlated with the response to clopidogrel (Lau W C et al.). CYP3A4 is reportedly responsible for the metabolism of most drugs and it has been believed that this pathway is a main limiting factor for biotransforming clopidogrel into its active metabolite.

However clopidogrel's metabolism may be influenced also by CYP2C19, CYP2C9 and possibly CYP3A5 (Brandt J T, Close S L et al. (2007) and Suh J H et al. (2006)). A number of well described genetic polymorphisms exist within the genes for these enzymes that render individuals either poor-metabolisers or ultra-metabolisers. For instance the common CYP2C19*2 allele displays a loss of function of this enzyme, and carriers have been reported to show a reduced antiplatelet response to 75 mg once daily of clopidogrel (Hulot J S et al. (2006) and Fontana P, Senouf D et al. (2007)) and a 300 mg loading dose (Brandt J T, Close S L et al (2007)). A CYP3A4 polymorphism has also been reported as associated with a reduced response to 300 mg of clopidogrel (Angiolillo D J et al. (2006); and Fontana P, Hulot J S et al (2006)). A CYP3A5 loss of function genotype *3 has been reported to be associated with increased atherothrombotic events in individuals after percutaneous coronary intervention (PCI) (Suh J H et al. (2006))

The pharmacokinetic component of the ISAR-CHOICE study suggested that the ceiling effect with clopidogrel 600 mg might be due to saturable intestinal absorption of the drug (von Beckerath N et al. (2005)). It was subsequently proposed that the p-glycoprotein efflux pump may be implicated in this process. Furthermore a polymorphism of the ABCB1 gene (C3435T), coding for p-glycoprotein, has been reported to reduce plasma parent drug levels (Taubert D et al.) However, this result has not been translated into a pharmacodynamic effect.

A lower pharmacodynamic response has reportedly been linked to a higher relative risk of adverse cardiac events in several clinical studies, suggesting that a reduced pharmacodynamic response to clopidogrel is clinically relevant (Ajzenberg, N, et al. (2005); Barragan, P et al. (2003); Cuisset, T et al. (2006); Gurbel, P A, Bliden, K P, Samara, W et al. (2005); Gurbel, P A, Bliden, K P, Guyer, K et al. (2005) and Matetzky, S et al. (2004)).

Response to clopidogrel displays wide inter-individual variability and a number of individuals show no or minimal response to the drug. Importantly, pharmacogenomic testing of patients in cardiovascular medicine is now entering clinical practice. The FDA has recently approved the pharmacogenetic testing of VKORC1 and CYP2C9 polymorphisms prior to warfarin therapy. Identifying poor responders or those at risk of bleeding with standard nomogram dosing may prevent drug related complications that account for a substantial proportion of morbidity in hospital patients.

It would be desirable and advantageous to have one or a combination of biomarkers which could be used to determine a subject's response to an antiplatelet agent, or the suitability of a subject to treatment with one or more antiplatelet agents using various doses and dose regimens. The present inventions provide such biomarkers and their use in methods to determine these phenotypic traits of a subject with respect to responses to antiplatelet drugs and drug treatment regimens.

BRIEF SUMMARY

The inventions described and claimed herein have many attributes and embodiments including, but not limited to, those set forth or described or referenced in this Brief Summary. It is not intended to be all-inclusive and the inventions described and claimed herein are not limited to or by the features or embodiments identified in this Brief Summary, which is included for purposes of illustration only and not restriction In one aspect, the invention is directed to determining in a subject the association between genotype(s) and drug response and/or suitability to a treatment regime.

Thus, according to one aspect there is provided a method of predicting or determining a subject's response to an antiplatelet agent, the method comprising analysing a sample from said subject for the presence or absence of one or more polymorphisms selected from the group consisting of:
1. 1A/G (rs28399504) in the gene encoding Cytochrome P450, family 2, subfamily C, polypeptide 19 (CYP2C19), also referred to as "CYP2C19*4", the "CYP2C19*4 genotype" or the "CYP2C19*4 carrier";
2. 636G>A in the gene encoding CYP2C19, also referred to as "CYP2C19*3", the "CYP2C19*3 genotype" or the "CYP2C19*3 carrier";
3. -806C/T (rs12248560) in the gene encoding CYP2C19, also referred to as "CYP2C19*17"; and,
4. 275A/G (rs1464602) in the gene encoding Nuclear receptor subfamily 1, group I, member 2 (NR1I2) (also referred to as BXR; PAR; PRR; PXR; SAR; SXR; ONR1; PAR1; PAR2; or PARq).

In one embodiment of the invention, the presence or absence of one or more of said polymorphisms is indicative of the subject's response to the antiplatelet agent. In one embodiment, the presence of one or more of said polymorphisms is generally indicative of a decreased response of a subject to an antiplatelet agent.

In another embodiment of the invention, one or both of the following polymorphisms may be utilized in conjunction with one or more or all of the above listed polymorphisms 1-5:
5. 6986G/A (rs776746) in the gene encoding Cytochrome P450, family 3, subfamily A, polypeptide 5 (CYP3A5), also referred to as "CYP3A5*1*1", the "CYP3A5*1*1 genotype" or the "CYP3A5*1*1 carrier"; and,
6. 31611T/C in the gene encoding CYP3A5.

These polymorphisms together may be referred to as "CYP3A5*1" (heterozygote) or "CYP3A5*1*1" (homozygote). In this embodiment, the presence of one or more of said polymorphisms is generally indicative of a decreased response of a subject to an antiplatelet agent. In another embodiment, the presence of one or more of said polymorphisms can be indicative of an increased response of a subject to an antiplatelet agent.

In another embodiment, the presence in a subject of polymorphisms CYP2C19*2, CYP2C19*3 and CYP2C19*4 will indicate an enhanced response of said subject to an increased dose, or increasing doses, of an antiplatelet agent. In one aspect, said subjects are non-responders or poor responders.

In one embodiment, the antiplatelet agent is selected from the thienopyridine class of antiplatelet agents. In one aspect of this embodiment, the antiplatelet agent is selected from the second generation class of thienopyridine antiplatelet agents. In one preferred embodiment, the antiplatelet agent is clopidogrel.

In another embodiment, the antiplatelet agent is selected from the third generation class of thienopyridine antiplatelet agents. In one preferred embodiment, the antiplatelet agent is prasugrel.

In another preferred embodiment, the antiplatelet agent is clopidogrel and the genotype of the individual includes one or more or all of CYP2C19*2, CYP2C19*3, CYP2C19*4 and CYP2C9*3, as described herein. In yet another preferred embodiment, the genotype of the subject includes 516G>T (rs3745274) TT or GT in the gene encoding CYP2B6, alone or together with one or more or all of the above polymorphisms. The presence of one or more of these polymophisms in an individual indicates a reduced response to clopidogrel.

In a particularly preferred embodiment, the antiplatelet agent is clopidogrel and the genotype of the individual includes CYP2C19*2 and CYP2C9*3. This combination of polymorphisms indicates a greater change in platelet inhibition in a subject following treatment with clopidogrel, including, for example, treatment with 150 mg daily.

In another preferred embodiment, the antiplatelet agent is clopidogrel and the genotype of the individual includes CYP2C19*17. This polymorphism indicates a greater change in platelet inhibition following treatment with clopidogrel.

The one or more polymorphisms can be detected directly or by detection of one or more polymorphisms which are in linkage disequilibrium with said one or more polymorphisms.

The method can additionally comprise analysing a sample from said subject for the presence of one or more further polymorphisms selected from the group consisting of:
7. 19154G/A (rs4244285) in the gene encoding CYP2C19, also referred to as "CYP2C19*2";
8. 42614A/C (rs1057910) in the gene encoding Cytochrome P450, family 2, subfamily C, polypeptide 9 (CYP2C9), also referred to as "CYP2C9*3; and
9. 516G>T (rs3745274) in the gene encoding Cytochrome P450, family 2, subfamily B, polypeptide 6, also referred to as "CYP2B6*9".

In this embodiment, the presence of one or more of said polymorphisms, alone or together with one or more or all of the above-noted polymorphisms is generally indicative of a decreased response of a subject to an antiplatelet agent. Again, detection of the one or more further polymorphisms may be carried out directly or by detection of polymorphisms in linkage disequilibrium with the one or more further polymorphisms.

The presence of one or more polymorphisms selected from the group consisting of: CYP3A5*1*1; CYP2C19*4;

CYP2C19*3; the −806C/T (rs12248560) TT or CT genotype in the gene encoding CYP2C19 (also referred to herein as a CYP2C19*17 genotype or CYP2C19*17 carrier); the 19154G/A (rs4244285) AA or GA genotype in the gene encoding CYP2C19 (also referred to herein as a CYP2C19*2 genotype or CYP2C19*2 carrier); the 42614A/C (rs1057910) CC or CA genotype in the gene encoding CYP2C9 (also referred to herein as a CYP2C9*3 genotype or CYP2C9*3 carrier); the 275A/G (rs1464602) GG or GA genotype in the gene encoding NR1I2; the 516G>T (rs3745274) TT or GT in the gene encoding CYP2B6, may be indicative of a poor response or resistance to the antiplatelet agent.

The presence of one or more polymorphisms selected from the group consisting of: CYP3A5*3*3; the 31611T/C TC or CC genotype in the gene encoding CYP3A5; the 1G/A (rs28399504) AA genotype in the gene encoding CYP2C19; the 636G>A (rs4986893) GG genotype in the gene encoding CYP2C19; the −806T>C (rs12248560) CC genotype in the gene encoding CYP2C19; the 19154A>G (rs4244285) GG genotype in the gene encoding CYP2C19; the 42614C>A (rs1057910) AA genotype in the gene encoding CYP2C9; or the 275G>A (rs1464602) AA genotype in the gene encoding NR1I2; the 516G>T (rs3745274) GG genotype in the gene encoding CYP2B6, may be indicative of responsiveness to the antiplatelet agent.

Preferably, the antiplatelet agent is a thienopyridine, more preferably clopidogrel.

The methods of the invention are particularly useful in subjects at risk of or suffering from a disease or condition associated with platelet aggregation, including coronary artery disease, acute coronary syndrome, peripheral vascular disease, atherosclerosis including symptomatic atherosclerosis, cerebrovascular diseases, thromboembolism, or subjects undergoing or who have undergone treatment for one or more of these diseases or conditions, including surgical treatment, including placement of stents, bypass surgery, valve replacement, and the like.

Where the following discussion refers to aspects of the invention useful to predict or determine a subject's response to one or more antiplatelet agents, it will be appreciated that these aspects of the invention are also useful in determining a subject's suitability for a treatment regime, preferably in determining a subject's suitability to prophylactic or therapeutic treatment with an antiplatelet agent, including anti-platelet agent is selected from the thienopyridine class of antiplatelet agents, including second generation thienopyridine antiplatelet agents (including clopidogrel), and third generation thienopyridine antiplatelet agents (including prasugrel).

It will be appreciated that the methods of the invention identifies several categories of polymorphisms or polymorphism combinations—namely those associated with poor response or resistance to one or more antiplatelet agents (referred to herein as "resistance polymorphisms"), those associated with response to one or more antiplatelet agents (referred to herein as "responsive polymorphisms"), those associated with response to one or more antiplatelet agent treatment regimens, and those associated with response to varying doses, including increased dosages, of one or more antiplatelet agent.

These SNPs can be aggregated into a scoring system that allows the stratification of an individual into a responder category i.e. responder, mildly reduced response, moderately reduced response or non-responder. Absence of any one of the identified resistance polymorphisms places an individual into the responder category.

Therefore, the present invention further provides a method of predicting or determining a subject's response to an antiplatelet agent, said method comprising:

determining the presence or absence of at least one resistance polymorphism associated with poor response or resistance to an antiplatelet agent;

wherein the presence of at least one resistance polymorphism is indicative of poor response or resistance to an antiplatelet agent.

Again, it will be appreciated that the above aspect may be used to determine a subject's suitability for a treatment regime or dosage, preferably in determining a subject's suitability to prophylactic or therapeutic treatment with an antiplatelet agent regime or dosage.

In one preferred form of the invention the presence of all of the responsive polymorphisms is indicative of a response to an antiplatelet agent.

In another preferred form of the invention the presence of two or more resistance polymorphisms is indicative of poor response or resistance to an antiplatelet agent.

In another aspect, the invention provides a method of predicting or determining a subject's response to an antiplatelet agent, said method comprising providing the result of one or more genetic tests of a sample from said subject, and analysing the result for the presence or absence of one or more polymorphisms selected from the groups described herein (or one or more polymorphisms in linkage disequilibrium with any one or more of these polymorphisms), or from the group consisting of: 6986G/A (rs776746) in the gene encoding CYP3A5; 31611T/C in the gene encoding CYP3A5; 1A/G (rs28399504) in the gene encoding CYP2C19; 636G>A (rs4986893) in the gene encoding CYP2C19; −806C/T (rs12248560) in the gene encoding CYP2C19; 275A/G (rs1464602) in the gene encoding NR1I2; or one or more polymorphisms in linkage disequilibrium with any one or more of these polymorphisms; wherein a result indicating the presence or absence of one or more of said polymorphisms is indicative of the subject's response to an antiplatelet agent.

In a further aspect there is provided a method of predicting or determining a subject's response to an antiplatelet agent comprising the analysis of two or more polymorphisms selected from the group consisting of 6986G/A (rs776746) in the gene encoding CYP3A5; 31611T/C in the gene encoding CYP3A5; 1A/G (rs28399504) in the gene encoding CYP2C19; 636 G>A (rs4986893) in the gene encoding CYP2C19; −806C/T (rs12248560) in the gene encoding CYP2C19; 275A/G (rs1464602) in the gene encoding NR1I2; or one or more polymorphisms in linkage disequilibrium with any one or more of these polymorphisms.

In one form of the invention the methods as described herein are performed in conjunction with an analysis of one or more risk factors, including one or more epidemiological risk factors, associated with a response to an antiplatelet agent. Such epidemiological risk factors include but are not limited to smoking or exposure to tobacco smoke, age, sex, and familial history of a disease or condition associated with platelet aggregation, including coronary artery disease, acute coronary syndrome, peripheral vascular disease, atherosclerosis including symptomatic atherosclerosis, cerebrovascular diseases, thromboembolism, or subjects undergoing or who have undergone treatment for one or more of these diseases or conditions, including surgical treatment, including placement of stents, bypass surgery, valve replacement, and the like.

In a further aspect, the invention provides for the use of at least one polymorphism in the assessment of a subject's response to an antiplatelet agent, wherein said at least one polymorphism is selected from the group consisting of: 6986G/A (rs776746) in the gene encoding CYP3A5; 31611T/C in the gene encoding CYP3A5; 1A/G (rs28399504) in the gene encoding CYP2C19; 636 G>A (rs4986893) in the gene encoding CYP2C19; −806C/T (rs12248560) in the gene encoding CYP2C19; 275A/G (rs1464602) in the gene encoding NR1I2; 516G>T (rs3745274) in the gene encoding CYP2B6; or one or more polymorphisms in linkage disequilibrium with any one of said polymorphisms.

Optionally, said use may be in conjunction with the use of at least one further polymorphism selected from the group consisting of: 19154G/A (rs4244285) in the gene encoding CYP2C19; 42614A/C (rs1057910) in the gene encoding CYP2C9; 516G>T (rs3745274) in the gene encoding CYP2B6; or one or more polymorphisms which are in linkage disequilibrium with any one or more of these polymorphisms.

In another aspect the invention provides a set of nucleotide probes and/or primers for use in the preferred methods of the invention herein described. Preferably, the nucleotide probes and/or primers are those which span, or are able to be used to span, the polymorphic regions of the genes. Also provided are one or more nucleotide probes and/or primers comprising the sequence of any one of the probes and/or primers herein described.

In yet a further aspect, the invention provides a nucleic acid microarray for use in the methods of the invention, which microarray comprises a substrate presenting nucleic acid sequences capable of hybridizing to nucleic acid sequences which encode one or more of the resistance or responsive polymorphisms described herein or sequences complementary thereto.

In another aspect, the invention provides an antibody microarray for use in the methods of the invention, which microarray comprises a substrate presenting antibodies capable of binding to a product of expression of a gene the expression of which is upregulated or downregulated when associated with a resistance or responsive polymorphism as described herein.

In still a further aspect, the present invention provides a method of assessing a subject's suitability for an intervention that is diagnostic of or therapeutic for a disease associated with platelet aggregation, the method comprising a) providing the result of one or more genetic tests of a sample from the subject, and b) analysing the result for the presence or absence of one or more responsive polymorphisms or for the presence or absence of one or more resistance polymorphisms, wherein said responsive or resistance polymorphisms are selected from the group consisting of 6986G/A (rs776746) in the gene encoding CYP3A5; 31611T/C in the gene encoding CYP3A5; 1A/G (rs28399504) in the gene encoding CYP2C19; 636G>A (rs4986893) in the gene encoding CYP2C19; −806C/T (rs12248560) in the gene encoding CYP2C19; 275A/G (rs1464602) in the gene encoding NR1I2; or one or more polymorphisms which are in linkage disequilibrium with any one or more of said polymorphisms; wherein the presence of one or more resistance polymorphisms is indicative of the subject's suitability or unsuitability for the intervention.

In one embodiment, the intervention is a diagnostic test for a disease or condition associated with platelet aggregation, including coronary artery disease, acute coronary syndrome, peripheral vascular disease, atherosclerosis including symptomatic atherosclerosis, cerebrovascular diseases, thromboembolism, or subjects undergoing or who have undergone treatment for one or more of these diseases or conditions, including surgical treatment, including placement of stents, bypass surgery, valve replacement, and the like.

In another embodiment, the intervention is a therapy for a disease or condition associated with platelet aggregation, including coronary artery disease, acute coronary syndrome, peripheral vascular disease, atherosclerosis including symptomatic atherosclerosis, cerebrovascular diseases, thromboembolism, or subjects undergoing or who have undergone treatment for one or more of these diseases or conditions, including surgical treatment, including placement of stents including a determination of whether a drug eluting or bare metal coronary stent is to be implanted, bypass surgery, valve replacement, and the like, more preferably a preventative therapy for said diseases or conditions.

Preferably, the method comprises an analysis for the presence or absence of one or more additional responsive or resistance polymorphisms selected from the group consisting of: 19154G/A (rs4244285) in the gene encoding CYP2C19; 42614A/C (rs1057910) in the gene encoding CYP2C9; 516G>T (rs3745274) in the gene encoding CYP2B6; or one or more polymorphisms which are in linkage disequilibrium with any one or more of these polymorphisms.

In a still further aspect, the invention provides for the use of data predictive of the responsiveness of a subject to an antiplatelet agent in the determination of the subject's suitability for an intervention that is diagnostic of or therapeutic for a disease or condition associated with platelet aggregation, said data comprising, consisting of or including the result of at least one antiplatelet agent response-associated genetic analysis selected from one or more of the genetic analyses described herein, and said data being indicative of the subject's suitability or unsuitability for the intervention.

For example, the determination is whether a drug eluting or bare metal coronary stent is to be implanted. In one embodiment, the data is representative of the presence of one or more responsive polymorphisms, or is representative of the absence of one or more responsive polymorphisms, or is representative of the presence of one or more resistance polymorphisms.

In another aspect, the invention provides a system for determining a subject's response to an antiplatelet agent, said system comprising: computer processor means for receiving, processing and communicating data; storage means for storing data including a reference genetic database of the results of at least one genetic analysis with respect to response to an antiplatelet agent or with respect to a disease or condition associated with platelet aggregation, and optionally a reference non-genetic database of non-genetic risk factors for a disease or condition associated with platelet aggregation; and a computer program embedded within the computer processor which, once data consisting of or including the result of a genetic analysis for which data is included in the reference genetic database is received, processes said data in the context of said reference databases to determine, as an outcome, the subject's response to an antiplatelet agent, said outcome being communicable once known, preferably to a user having input said data.

Preferably, the at least one genetic analysis is an analysis of one or more polymorphisms selected from the group consisting of: 6986G/A (rs776746) in the gene encoding CYP3A5; 31611T/C in the gene encoding CYP3A5; 1A/G (rs28399504) in the gene encoding CYP2C19; 636G>A (rs4986893) in the gene encoding CYP2C19; −806C/T (rs12248560) in the gene encoding CYP2C19; or 275A/G (rs1464602) in the gene encoding NR1I2; one or more polymorphisms which are in linkage disequilibrium with said one or more polymorphisms.

In one embodiment, the data is input by a representative of a healthcare provider. In another embodiment, the data is input by the subject, their medical advisor or other representative. Preferably, said system is accessible via the internet or by personal computer.

Preferably, said reference genetic database consists of, comprises or includes the results of an antiplatelet agent response-associated genetic analysis selected from one or more of the genetic analyses described herein, preferably the results of an analysis of one or more polymorphisms selected from the group consisting of: 6986G/A (rs776746) in the gene encoding CYP3A5; 31611T/C in the gene encoding CYP3A5; 1A/G (rs28399504) in the gene encoding CYP2C19; 636G>A (rs4986893) in the gene encoding CYP2C19; −806C/T (rs12248560) in the gene encoding CYP2C19; 275A/G (rs1464602) in the gene encoding NR1I2; 19154G/A (rs4244285) in the gene encoding CYP2C19; 42614A/C (rs1057910) in the gene encoding CYP2C9; or one or more polymorphisms which are in linkage disequilibrium with said one or more polymorphisms.

More preferably, said reference genetic database consists of, comprises or includes the results of an analysis of any two, any three, any four, or all of the polymorphisms selected from the group consisting of: 6986G/A (rs776746) in the gene encoding CYP3A5; 31611T/C in the gene encoding CYP3A5; 1A/G (rs28399504) in the gene encoding CYP2C19; 636G>A (rs4986893) in the gene encoding CYP2C19; −806C/T (rs12248560) in the gene encoding CYP2C19; or 275A/G (rs1464602) in the gene encoding NR1I2. The reference genetic database may additionally comprise or include the results of an analysis of one or more further polymorphisms selected from the group consisting of: 19154G/A (rs4244285) in the gene encoding CYP2C19; 516G>T (rs3745274) in the gene encoding CYP2B6; or 42614A/C (rs1057910) in the gene encoding CYP2C9. More preferably, said reference genetic database consists of, comprises or includes the results of all of the genetic analyses described herein.

In yet a further aspect, the invention provides a computer program suitable for use in a system as defined above comprising a computer usable medium having program code embodied in the medium for causing the computer program to process received data consisting of or including the result of at least one antiplatelet agent response-associated genetic analysis in the context of both a reference genetic database of the results of said at least one antiplatelet agent response-associated genetic analysis and optionally a reference non-genetic database of non-genetic risk factors for a disease or condition associated with platelet aggregation.

Preferably, the at least one antiplatelet agent response-associated genetic analysis is selected from one or more of the genetic analyses described herein, preferably the at least one antiplatelet agent response-associated genetic analysis is an analysis of one or more polymorphisms selected from the group consisting of: 6986G/A (rs776746) in the gene encoding CYP3A5; 31611T/C in the gene encoding CYP3A5; 1A/G (rs28399504) in the gene encoding CYP2C19; 636 G>A (rs4986893) in the gene encoding CYP2C19; −806C/T (rs12248560) in the gene encoding CYP2C19; 275A/G (rs1464602) in the gene encoding NR1I2; or one or more polymorphisms which are in linkage disequilibrium with said one or more polymorphisms. Preferably, the at least one antiplatelet agent response-associated genetic analysis is an analysis of any two, any three, any four, or all of the polymorphisms selected from this group.

The at least one antiplatelet agent response-associated genetic analysis can additionally comprise the analysis of one or more further polymorphisms selected from the group consisting of: 19154G/A (rs4244285) in the gene encoding CYP2C19; 516G>T (rs3745274) in the gene encoding CYP2B6; or 42614A/C (rs1057910) in the gene encoding CYP2C9.

Preferably, the at least one antiplatelet agent response-associated genetic analysis is an analysis of the genetic analyses described herein.

Also provided are computer systems and programs as described above for the determination of the subject's suitability for an intervention that is diagnostic of or therapeutic for a disease or condition associated with platelet aggregation.

In a still further aspect, the invention provides for the use of data predictive of the predisposition of a subject to a disease or condition associated with platelet aggregation in the prediction or determination of the subject's response to an antiplatelet agent, said data comprising, consisting of or including the result of at least one antiplatelet agent response-associated genetic analysis selected from one or more of the genetic analyses described herein, and said data being representative of the subject's response to an antiplatelet agent. Preferably, the data comprises, consists of or includes the result of an analysis of one or more polymorphisms selected from the group consisting of: 6986G/A (rs776746) in the gene encoding CYP3A5; 31611T/C in the gene encoding CYP3A5; 1A/G (rs28399504) in the gene encoding CYP2C19; −806C/T (rs12248560) in the gene encoding CYP2C19; 275A/G (rs1464602) in the gene encoding NR1I2; 636 G>A (rs4986893) in the gene encoding CYP2C19; or one or more polymorphisms which are in linkage disequilibrium with said one or more polymorphisms More preferably, the data comprises, consists of or includes the results of an analysis of two or more, three or more, four or more, or all of the above polymorphisms. More preferably, the data comprises, consists of or includes the results of all of the genetic analyses described herein.

In a further aspect, the present invention provides a kit for assessing a subject's response to an antiplatelet agent, said kit comprising a means of analysing a sample from said subject for the presence or absence of one or more polymorphisms disclosed herein.

In still a further aspect, the present invention provides a method of assessing a subject's suitability for a therapeutic intervention for a disease associated with platelet aggregation, the method comprising: a) providing the result of one or more tests of platelet inhibition in a sample from the subject; and b) analysing the result; wherein a result indicative of less than about 10% platelet inhibition is indicative of the subject's suitability or unsuitability for the intervention.

Preferably, the therapeutic intervention is treatment with, for example, clopidogrel. Alternatively, the therapeutic intervention is treatment with prasugrel.

Preferably, the test of platelet inhibition is a test of platelet inhibition after administration of clopidogrel, preferably a test of platelet inhibition at about two hours after administration of clopidogrel.

Preferably the test of platelet inhibition is measured using a rapid platelet function analyser, more preferably the VerifyNow rapid platelet function analyser, more preferably the VerifyNow rapid platelet function analyser together with a P2Y12 cartridge.

In one embodiment, a result of less than about 5% platelet inhibition, of less than about 4% platelet inhibition, of less than about 3% platelet inhibition, or preferably of less than about 2% platelet inhibition, is indicative of the subject's unsuitability for the therapeutic intervention, more preferably is indicative of the subject's unsuitability for treatment with clopidogrel.

In another embodiment, a result of less than about 5% platelet inhibition, of less than about 4% platelet inhibition, of less than about 3% platelet inhibition, or preferably of less than about 2% platelet inhibition, is indicative of the subject's suitability for the therapeutic intervention, more preferably is indicative of the subject's suitability for treatment with prasugrel.

In another embodiment, a result of less than about 10% platelet inhibition, of less than about 5% platelet inhibition, of less than about 4% platelet inhibition, of less than about 3% platelet inhibition, or preferably of less than about 2% platelet inhibition, is indicative of the subject's suitability for the therapeutic intervention, more preferably is indicative of the subject's suitability for a high dosage treatment regimen of clopidogrel, more preferably more preferably is indicative of the subject's suitability for a high dosage treatment regimen of clopidogrel comprising administration of clopidogrel at a loading dose of about 1200 mg and a daily maintenance dose of about 150 mg.

In a further aspect there is provided a method of predicting or determining the efficacy of a treatment regimen of a subject for a disease associated with platelet aggregation, wherein the treatment regimen comprises administration of an antiplatelet agent, the method comprising a) providing the result of one or more tests of platelet inhibition in a sample from the subject; and b) analysing the result; wherein a result indicative of less than about 10% platelet inhibition is indicative of reduced efficacy of the treatment regimen.

Preferably, the efficacy is long-term efficacy, more preferably the efficacy of the treatment regimen after one week of treatment, after one month of treatment, or after between about one month and one year of treatment.

Preferably, the antiplatelet agent is, for example, clopidogrel.

Preferably the treatment regimen comprises administration of clopidogrel at a loading dose of about 600 mg and a daily maintenance dose of about 75 mg.

Preferably, the test of platelet inhibition is a test of platelet inhibition after administration of clopidogrel, preferably a test of platelet inhibition at about two hours after administration of clopidogrel.

Preferably the test of platelet inhibition is measured using a rapid platelet function analyser, more preferably the VerifyNow rapid platelet function analyser, more preferably the VerifyNow rapid platelet function analyser together with a P2Y12 cartridge.

In one embodiment, a result of less than about 5% platelet inhibition, of less than about 4% platelet inhibition, of less than about 3% platelet inhibition, or preferably of less than about 2% platelet inhibition, is indicative of reduced efficacy of the treatment regimen, more preferably is indicative of reduced efficacy of treatment with clopidogrel, more preferably is indicative of reduced efficacy of treatment with clopidogrel at a loading dose of about 600 mg and a daily maintenance dose of about 75 mg.

In still a further aspect, the present invention provides a method of treating a disease associated with platelet aggregation in a subject, the method comprising: a) administering to the subject a loading dosage of clopidogrel on the first day of treatment, the loading dose being in the range of from above 600 mg to about 1800 mg; b) administering to the subject a maintenance dosage of clopidogrel on each subsequent day of treatment, the maintenance dosage being in the range of from above 50 mg to about 200 mg.

In a preferred embodiment, the loading dose is in the range of from above 600 mg to about 1500 mg, more preferably in the range of from above 900 mg to about 1500 mg, more preferably the loading dose is about 1200 mg.

In a preferred embodiment, the maintenance dosage is between about 50 mg and about 200 mg, more preferably between about 75 mg and about 150 mg, more preferably the daily maintenance dose is about 150 mg.

Preferably, the subject has been identified as a clopidogrel non-responder or poor responder, more preferably the subject has been identified as a clopidogrel non-responder or poor responder using a method of the present invention.

In another aspect, the present invention provides a method of treating a disease associated with platelet aggregation in a subject, the method comprising: a) administering to the subject a first loading dosage of clopidogrel on the first day of treatment, the first loading dose being in the range of from above 300 mg to about 900 mg; b) administering to the subject a second loading dosage of clopidogrel on the first day of treatment, the second loading dose being in the range of from above 300 mg to about 900 mg; c) administering to the subject a maintenance dosage of clopidogrel on each subsequent day of treatment, the maintenance dosage being in the range of from above 50 mg to about 200 mg; wherein the second loading dose is administered at least about 30 minutes after the first loading dose.

In a preferred embodiment, the first loading dose is 600 mg. In another preferred embodiment, the second loading dose is 600 mg.

Preferably, the second loading dose is administered at between about 30 min to 4 hours after the first loading dose, preferably between about 45 min and 3 hours after the first loading dose, more preferably between about 1 hour and about 2.5 hours, more preferably about 2 hours after the first loading dose.

In a preferred embodiment, the maintenance dosage is between about 50 mg and about 200 mg, more preferably between about 75 mg and about 150 mg, more preferably the daily maintenance dose is about 150 mg.

The invention further provides an article of manufacture comprising a plurality of dosage forms comprising clopidogrel and instructions for administering the clopidogrel to a patient suffering from a disease associated with platelet aggregation, wherein the instructions provide that clopidogrel is administered in accordance with a method of treatment of the present invention as described above.

Preferably, the instructions provide that clopidogrel is administered in a loading dose of about 1200 mg on the first day of the treatment, followed by a maintenance dose of about 150 mg on each subsequent day of treatment.

Preferably, the plurality of dosage forms comprise at least one loading dose dosage form and at least one maintenance dose dosage form, the at least one loading dose dosage form providing a total dosage of about 1200 mg, and the maintenance dose dosage form comprising about 150 mg.

Preferably, the instructions provide that clopidogrel is administered in a first loading dose of about 600 mg on the first day of the treatment, and that clopidogrel is administered in a second loading dosage of about 600 mg at least about 30 minutes after the first loading dose, and that a maintenance dosage of about 150 mg clopidogrel is administered on each subsequent day of treatment.

Preferably, the plurality of dosage forms comprise at least two loading dose dosage forms and at least one maintenance dose dosage form, the at least two loading dose dosage form providing a total dosage of about 1200 mg clopidogrel, and the maintenance dose dosage form comprising about 150 mg clopidogrel. Preferably, the at least two loading dose dosage forms each comprise about 600 mg clopidogrel.

Preferably, the dosage forms are oral dosage forms.

The use of clopidogrel in the preparation of a medicament or dosage form suitable for use in the above methods is also provided

| Gene | Polymorphism | Rs# | Genotype | Phenotype |
| --- | --- | --- | --- | --- |
| CYP3A5*1*1 | 6986G > A and 31611T > C | rs776746 | AA and CC | resistance |
| CYP3A5*3*3 | 6986A > G | rs776746 | AG or GG | responsive |
| CYP2C19*2 | 19154G > A | rs4244285 | AA or GA | resistance |
| CYP2C19*3 | 636G > A | rs4986893 | AA or GA | resistance |
| CYP2C19*4 | 1A > G | rs28399504 | GG or GA | resistance |
| CYP2C19*17 | −806G > T | rs12248560 | TT or CT | resistance or responsive |
| CYP2C19*1 | 1G > A | rs28399504 | AA | responsive |
|  | −806T > C | rs12248560 | CC | responsive |
|  | 19154A > G | rs4244285 | GG | responsive |
| CYP2C9*3 | 42614A > C | rs1057910 | CC or CA | resistance |
| CYP2C9*1 | 42614C > A | rs1057910 | AA | responsive |
| CYP2B6*9 | 516G > T | rs3745274 | TT or TG | resistance |
| NR1I2 | 275A > G | rs1464602 | GG or GA allele | resistance |
|  | 275G > A | rs1464602 | AA allele | responsive |

Figure 3:
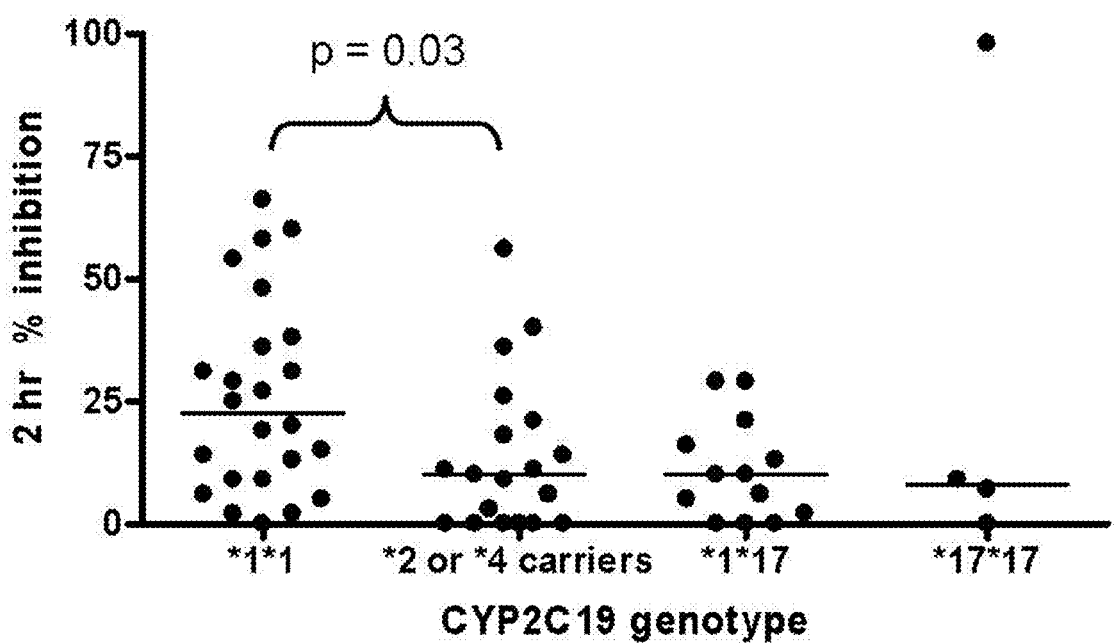

FIG. 3 shows platelet inhibition two hours after clopidogrel 600 mg. CYP2C19*2 and CYP2C19*4 carriers display loss of function of the CYP2C19 enzyme, whereas CYP2C19*17 represent gain of function. P value calculated using Kruskal-Wallis test.

Figure 4:
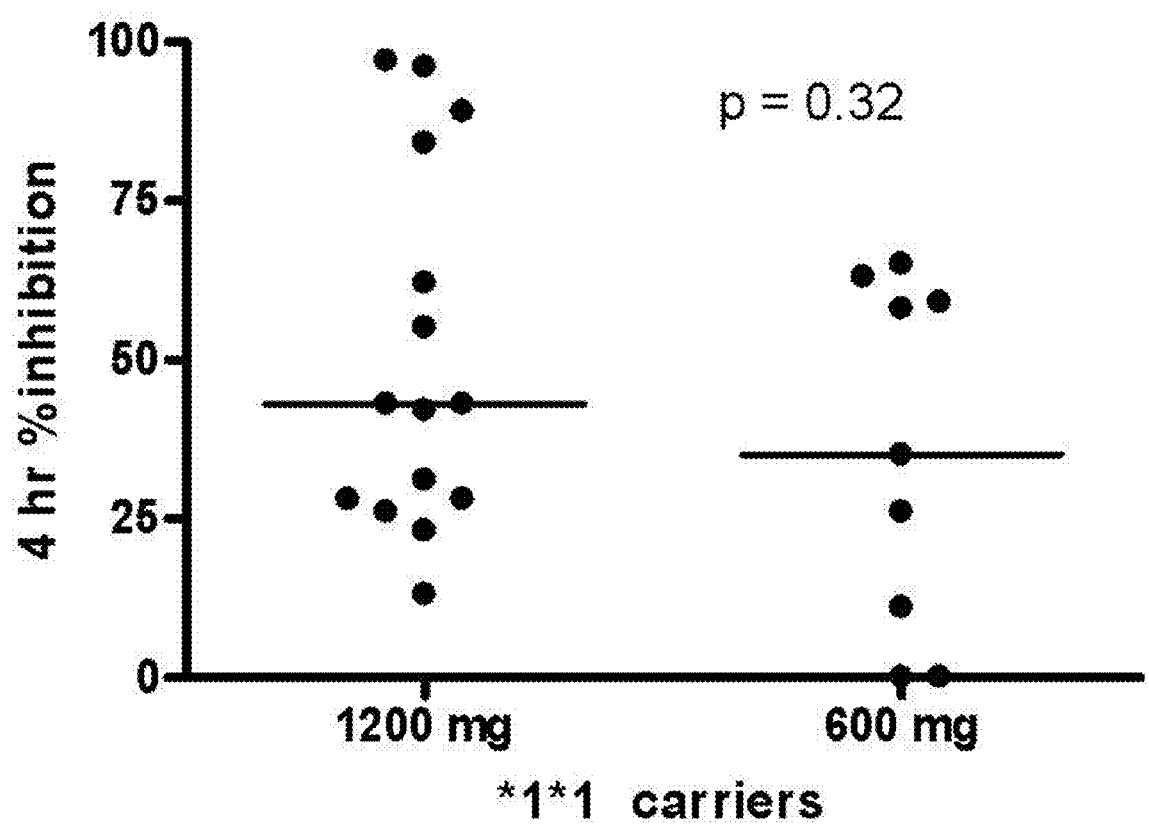

FIG. 4 shows platelet inhibition two hours after second clopidogrel loading dose in CYP2C19*1*1 normal carriers. *1 carriers display normal CYP2C19 enzyme function. P value calculated using Mann Whitney test.

Figure 5:
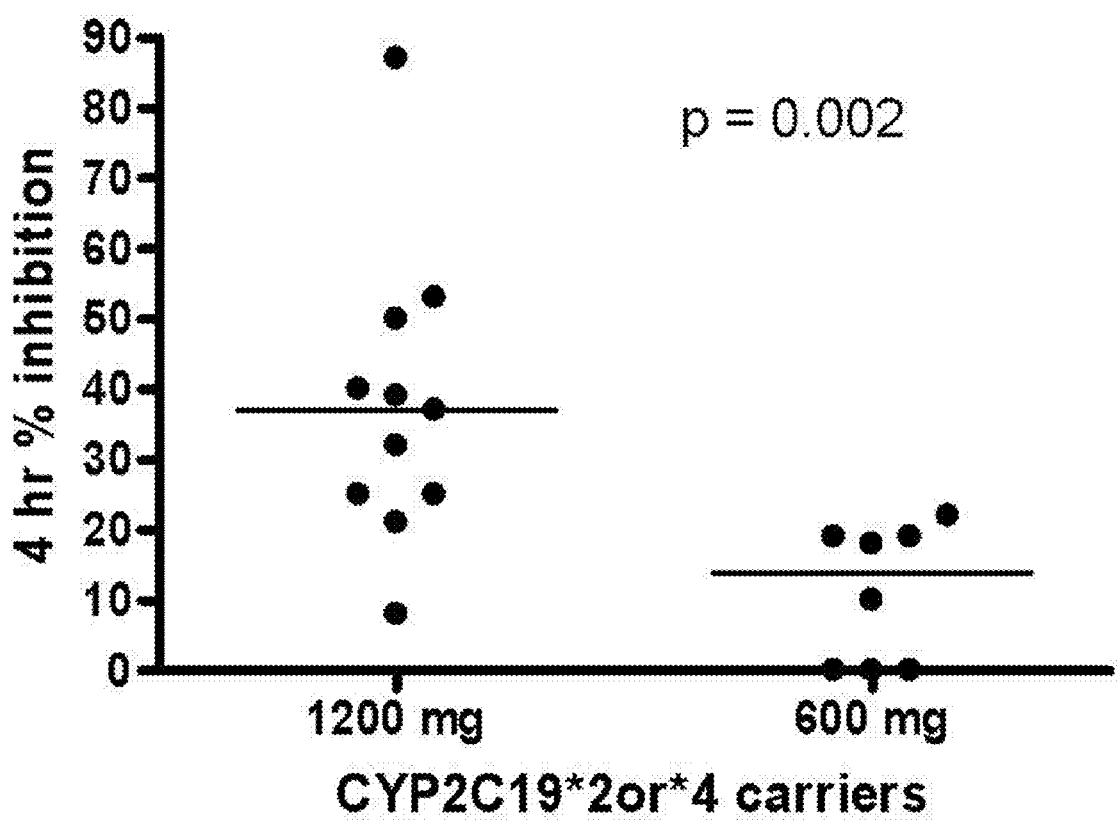

FIG. 5 shows platelet inhibition two hours after second clopidogrel loading dose in CYP2C19*2 or *4 loss of function carriers.

Figure 6:
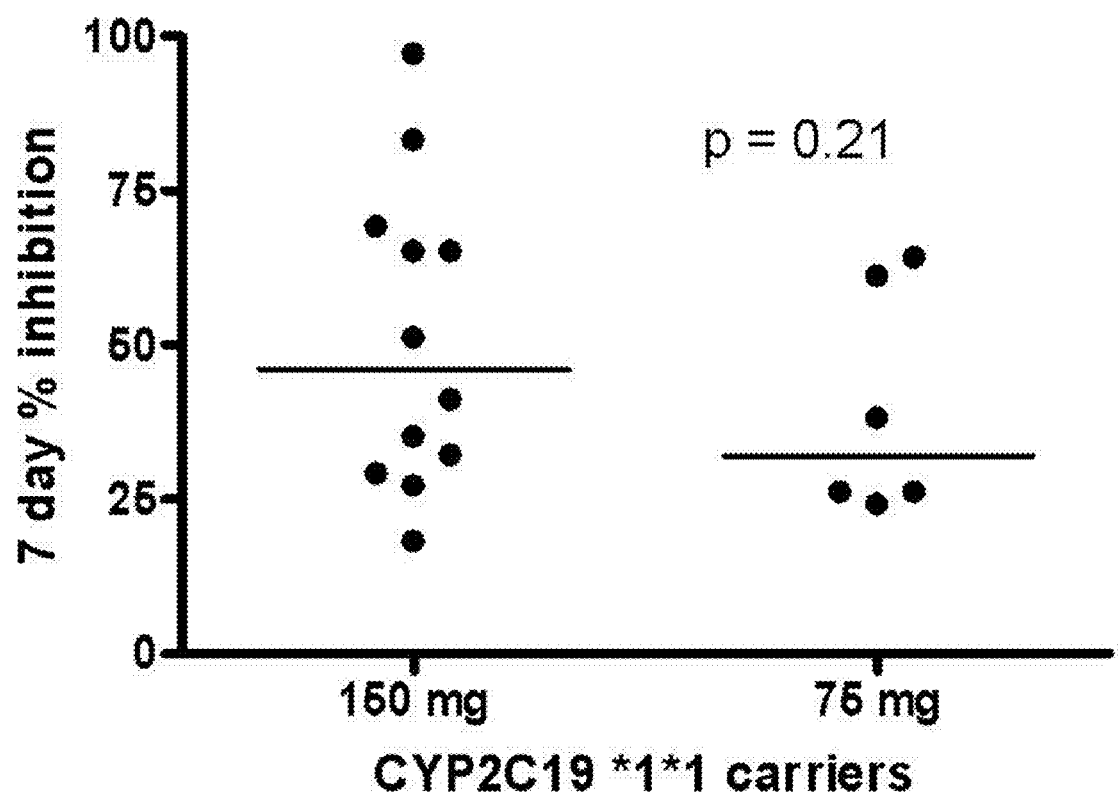

FIG. 6 shows platelet inhibition at seven days in CYP2C19 normal carriers.

Figure 7:
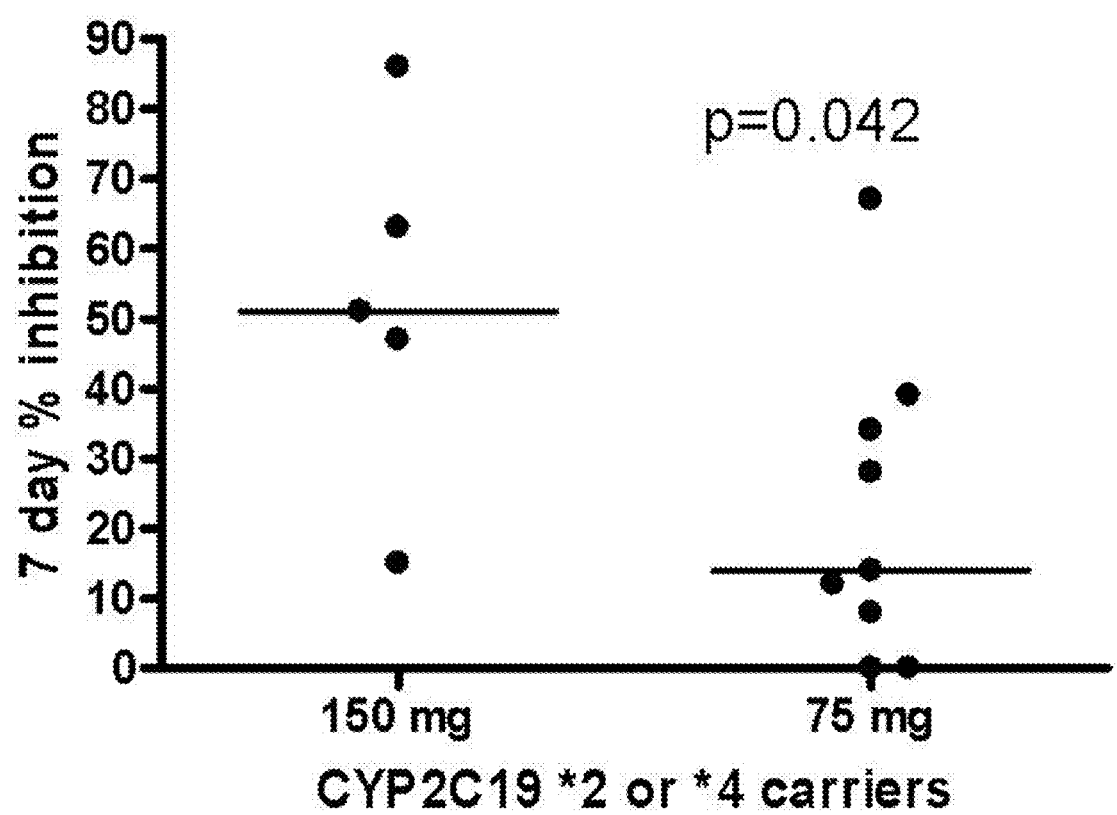

FIG. 7 shows platelet inhibition at 7 days in CYP2CIP*2 or *4 loss of function carriers.

Figure 8:
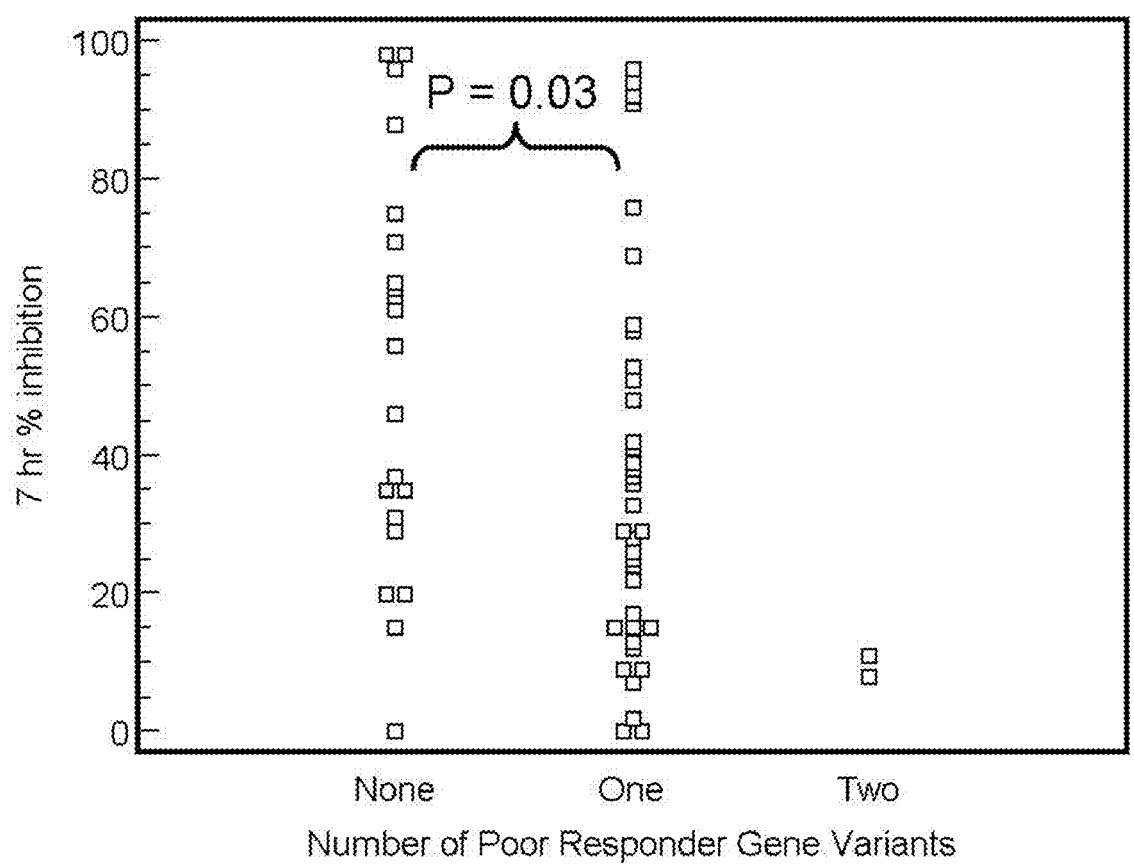

FIG. 8 shows additive effects of poor responder genotypes (CYP2C19 and CYP2C9) across all individuals irrespective of dose. P value calculated using Wilcoxon test.

Figure 9:
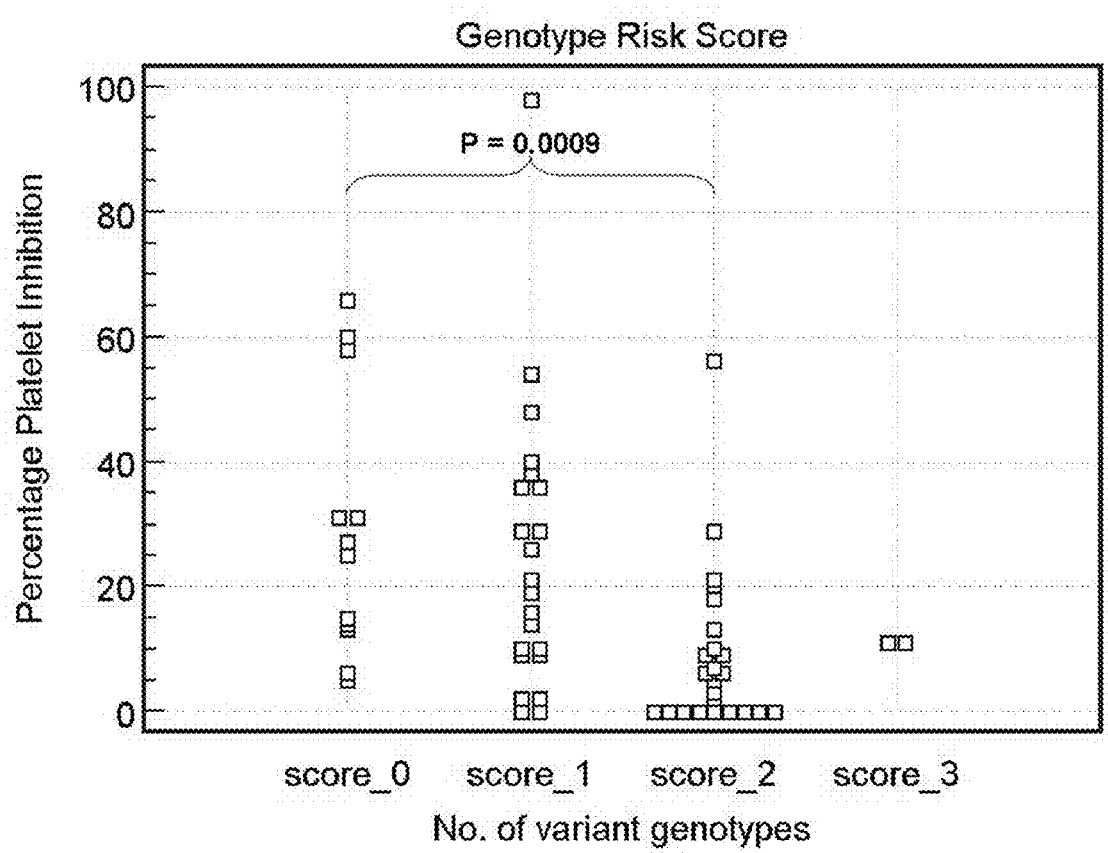

FIG. 9 shows genotype risk score for clopidogrel responder status, where the number of resistance genotypes is plotted against platelet inhibition at two hours. P value calculated by Wilcoxon test.

DESCRIPTION OF THE PREFERRED EMBODIMENTS

The terms pharmacogenetics and pharmacogenomics and grammatical equivalents thereof are used interchangeably herein. These terms refer to the study of how an individual's genes determine his or her response to a drug (e.g., a patient's "drug response phenotype", or "drug response genotype".) Pharmacogenomics allows a clinician or physician to target prophylactic or therapeutic treatments to patients, for example to those who will most benefit from the treatment, or to avoid treatment of patients who will experience toxic drug-related side effects or decreased or no efficacy.

Using case-control studies the frequencies of several genetic variants (polymorphisms) of candidate genes in subjects undergoing coronary interventions have been compared. The majority of these candidate genes have confirmed (or likely) functional effects on gene expression or protein function. Specifically, the frequencies of polymorphisms between subjects with poor drug response and those with good drug response have been compared.

In one embodiment described herein both resistance genetic polymorphisms and responsive genetic polymorphisms are identified. These are as follows:

A resistance genetic polymorphism (also referred to herein as a resistance polymorphism) is one which, when present, is indicative of poor response or resistance to an antiplatelet agent. In contrast, a responsive genetic polymorphism (also referred to herein as a responsive polymorphism) is one which, when present, is indicative of a response to an antiplatelet agent.

As used herein, the term "response" when used in reference to an antiplatelet agent means the susceptibility of the subject to the effect(s) of an antiplatelet agent and refers to the efficacy of the agent in said subject.

Accordingly, the phrase "a response to an antiplatelet agent" means that a subject having such a response possesses an hereditary inclination or tendency to respond to an antiplatelet agent, or that the subject exhibits a susceptibility to the effect(s) of an antiplatelet agent, such that the antiplatelet agent has efficacy. This does not necessarily mean that such a person will always respond to a given antiplatelet agent at any time, merely that he or she has a greater likelihood of responding compared to the general population of individuals that either possess a polymorphism associated with poor response or resistance or do not possess a polymorphism associated with a response to an antiplatelet agent (referred to herein as a responsive polymorphism).

Similarly, the phrase "poor response or resistance to an antiplatelet agent" means that a subject having such a poor response or resistance possesses an hereditary disinclination or reduced tendency to respond to an antiplatelet agent, or that the subject exhibits a decreased susceptibility to the effect(s) of an antiplatelet agent, such that the antiplatelet agent has decreased or no efficacy. Accordingly, poor response or resistance includes non-response. This does not necessarily mean that such a person will never respond to a given antiplatelet agent at any time, merely that he or she has a greater likelihood of not responding compared to the general population of individuals that either does not possess a polymorphism associated with poor response or resistance or does possess a polymorphism associated with a response to an antiplatelet agent (referred to herein as a responsive polymorphism).

A subject's response to an antiplatelet agent may be determined by analysing a sample from said subject for the presence or absence of a polymorphism selected from the group consisting of: 6986G/A (rs776746) in the gene encoding Cytochrome P450, family 3, subfamily A, polypeptide 5 (CYP3A5); 31611T/C in the gene encoding CYP3A5; 1A/G (rs28399504) in the gene encoding Cytochrome P450, family 2, subfamily C, polypeptide 19 (CYP2C19); 636G>A in the gene encoding Cytochrome P450, family 2, subfamily C, polypeptide 19 (CYP2C19); −806C/T (rs12248560) in the gene encoding CYP2C19; 275A/G (rs1464602) in the gene encoding NR1I2; or one or more polymorphisms which are in linkage disequilibrium with any one or more of the above group.

These polymorphisms can also be analysed in combinations of two or more, or in combination with other polymorphisms indicative of a subject's response to an antiplatelet agent, inclusive of the remaining polymorphisms listed above. In particular, these polymorphisms can be analysed in combination with one or more polymorphisms selected from the group consisting of: 19154G/A (rs4244285) in the gene encoding CYP2C19; 42614A/C (rs1057910) in the gene encoding Cytochrome P450, family 2, subfamily C, polypeptide 9 (CYP2C9); or 516G>T (rs3745274) in the gene encoding Cytochrome P450, family 2, subfamily B, polypeptide 6;

Assays which involve combinations of polymorphisms, including those amenable to high throughput, such as those utilising microarrays, are preferred.

Accordingly, in one aspect there is provided a method of predicting or determining a subject's response to an antiplatelet agent, the method comprising analysing a sample from said subject for the presence or absence of one or more polymorphisms selected from the group consisting of: 6986G/A (rs776746) in the gene encoding CYP3A5; 31611T/C in the gene encoding CYP3A5; 1A/G (rs28399504) in the gene encoding CYP2C19; 636 G/A (rs4986893) in the gene encoding CYP2C19; −806C/T (rs12248560) in the gene encoding CYP2C19; 275A/G (rs1464602) in the gene encoding NR1I2. wherein the presence or absence of one or more of said polymorphisms is indicative of the subject's response to the antiplatelet agent.

The one or more polymorphisms can be detected directly or by detection of one or more polymorphisms which are in linkage disequilibrium with said one or more polymorphisms.

Linkage disequilibrium (LD) is a phenomenon in genetics whereby two or more mutations or polymorphisms are in such close genetic proximity that they are co-inherited. This means that in genotyping, detection of one polymorphism as present infers the presence of the other. (Reich D E et al; Linkage disequilibrium in the human genome, Nature 2001, 411:199-204.)

The method can additionally comprise analysing a sample from said subject for the presence of one or more further polymorphisms selected from the group consisting of: 19154G/A (rs4244285) in the gene encoding CYP2C19; 42614A/C (rs1057910) in the gene encoding Cytochrome P450, family 2, subfamily C, polypeptide 9 (CYP2C9); 516G/T (rs3745274) in the gene encoding CYP2B6; Again, detection of the one or more further polymorphisms may be carried out directly or by detection of polymorphisms in linkage disequilibrium with the one or more further polymorphisms. The presence of one or more polymorphisms selected from the group consisting of: 1A>G (rs28399504) in the gene encoding CYP2C19; 636 G>A (rs4986893) in the gene encoding CYP2C19; −806C>T (rs12248560) in the gene encoding CYP2C19; 19154G>A (rs4244285) in the gene encoding CYP2C19; 42614A>C (rs1057910) in the gene encoding CYP2C9; 275A>G (rs1464602) in the gene encoding NR1I2; 516G>T (rs3745274) in the gene encoding CYP2B6; may be indicative of a poor response or resistance to the antiplatelet agent.

The effect of these SNPs on resistance to drug response is additive, so that the presence of two resistance polymorphisms is indicative of greater resistance than that indicated by the presence of one resistance polymorphism, three greater than two, and so on. SNPs within the same gene are not additive, whereby if gene function is reduced by one SNP, the addition of a second different SNP in the same gene does not further reduce function. The presence or absence of the resistance polymorphisms can therefore be combined into a score that categorises an individual, on a probabilistic basis, into responder status. For example, the following genotypes are all assigned a resistance value, in the present case, of +1 (where it will be appreciated that a negative value could also be assigned, provided all resistance polymorphism are assigned a negative value):

the 1A/G (rs28399504) GG or GA genotype in the gene encoding CYP2C19 (also referred to herein as a CYP2C19*4 genotype or CYP2C19*4 carrier); the −806C/T (rs12248560) TT or CT genotype in the gene encoding CYP2C19 (also referred to herein as a CYP2C19*17 genotype or CYP2C19*17 carrier); the 636G/A (rs4986893) AA or AG genotype in the gene encoding CYP2C19 (also referred to herein as a CYP2C19*3 genotype or CYP2C19*3 carrier); the 19154G/A (rs4244285) AA or GA genotype in the gene encoding CYP2C19 (also referred to herein as a CYP2C19*2 genotype or CYP2C19*2 carrier); the 42614A/C (rs1057910) CC or CA genotype in the gene encoding CYP2C9 (also referred to herein as a CYP2C9*3 genotype or CYP2C9*3 carrier); the 275A/G (rs1464602) GG or GA genotype in the gene encoding NR1I2; 516G>T (rs3745274) TT or GT in the gene encoding CYP2B6 (also referred to herein as a CYP2B6*9 genotype);

Responder status may then be determined as follows. The absence of any of the above genotypes (equivalent to a total score of 0 in the exemplary scoring) identifies the subject as a responder. The presence of one resistance genotype (equivalent to a total score of 1 in the exemplary scoring) identifies the subject as having mildly reduced response, while the presence of two resistance genotypes (equivalent to a total score of 2 in the exemplary scoring) identifies the subject as having moderately reduced response. The presence of three or four resistance genotype (equivalent to a total score of 3 or 4 in the exemplary scoring) identifies the subject as a nonresponder.

It will be appreciated that such a scoring system can be used to determine a suitable treatment regime for a subject. For example, a score of 0 indicates that treatment with, for example, clopidogrel, is suitable. Scores of 1 or 2 indicate that a higher dose of clopidogrel or alternative antiplatelet agent such as prasugrel should be considered, while a score ≧3 indicates that an alternative antiplatelet agent, such as prasugrel, should be considered. The presence of one or more polymorphisms selected from the group consisting of: the 1G/A (rs28399504) in the gene encoding CYP2C19; the 636G>A (rs4986893) in the gene encoding CYP2C19; the 19154A>G (rs4244285) in the gene encoding CYP2C19; the 636G>A (rs4986893) in the gene encoding CYP2C19, also referred to as "CYP2C19*3"; the 42614C>A (rs1057910) in the gene encoding CYP2C9; the 275G>A (rs1464602) in the gene encoding NR1I2; or the 516G>T (rs3745274) in the gene encoding CYP2B6 may be indicative of responsiveness to the antiplatelet agent. Presence of the −806T>C (rs12248560) in the gene encoding CYP2C19 may be scored as minus one.

It will be apparent that, using the exemplary scoring system described above, the above responsive polymorphisms may each be assigned a value of 0.

Statistical analyses, particularly of the combined effects of these polymorphisms, show that the genetic assays of the present invention can be used to determine the suitability of any subject to a treatment regime, preferably prophylactic or therapeutic treatment with an antiplatelet agent, and in particular to identify subjects with poor response or resistance to an antiplatelet agent. Such combined analysis can be of combinations of resistance polymorphisms only, of responsive polymorphisms only, or of combinations of both. Analysis can also be step-wise, with analysis of the presence or absence of responsive polymorphisms occurring first and then with analysis of resistance polymorphisms proceeding only where no responsive polymorphisms are present.

Thus, through systematic analysis of the frequency of these polymorphisms in well defined groups of subjects as described herein, it is possible to implicate certain genes and proteins in the response to an antiplatelet agent and improve the ability to identify which subjects have poor response or resistance to an antiplatelet agent, and to identify those subjects who would benefit from a particular treatment regime.

Thus, another aspect of the invention provides methods for tailoring an individual's prophylactic or therapeutic treatment with one or more agents, preferably one or more antiplatelet agents according to that individual's drug response genotype.

Antiplatelet Agents

As used herein, the term "antiplatelet agent" and grammatical equivalents thereof refers to an agent, including a drug, compound, biologic or combination thereof, that diminishes or abrogates platelet aggregation.

Antiplatelet agents have a variety of mechanisms of action, Platelets are activated by a number of physiological agonists including thromboxane, adenosine diphosphate (ADP), thrombin, serotonin and collagen. Shear stress, a physical property of blood flow, also plays an important role. Platelets are capable of inducing their own aggregation, predominantly via thrombin generation, leading to an amplification reaction.

Figure 1:
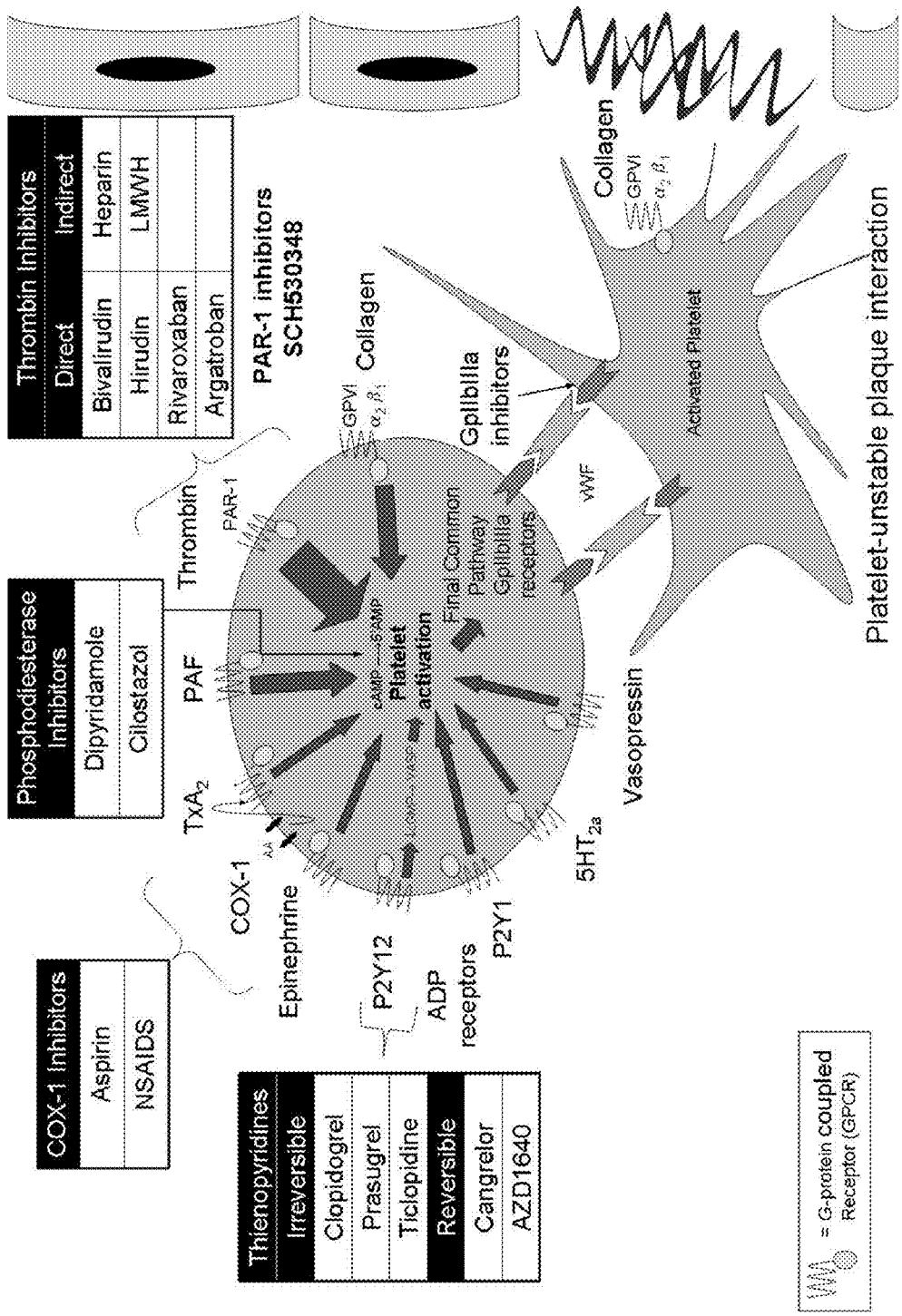
FIG. 1 shows agonists to platelet activation and antiplatelet agents.

Despite the wide range of platelet agonists, only four pathways are targeted by drugs in the marketplace and are well known in the art; as shown in FIG. 1. There are thromboxane pathway inhibitors such as aspirin and non-steroidal anti-inflammatory drugs, P2Y12 receptor antagonists such as the thienopyridines ticlopidine, clopidogrel and prasugrel, phosphodiesterase inhibitors such as dipyridamole and cilostazol, and glycoprotein IIb/IIIa inhibitors including abciximab, eptifibatide and tirofiban.

In certain embodiments, an antiplatelet agent to which the invention is directed is an antiplatelet agent that is metabolised or otherwise cleared by a gene product encoded by one or more of the group of genes comprising CYP3A5, CYP2C19, CYP2C9, CYP2B6*9, and NR1I2.

The thienopyridines are pro-drugs that are converted in vivo to active metabolites that react with and irreversibly inhibit the platelet P2Y12 adenosine diphosphate (ADP) receptor, which is involved in platelet activation and stabilization of the platelet aggregate [Savi, P, Herbert J M (2005); Sugidachi, A et al., (2000); Goto, S et al. (2006) and Cattaneo, M (2003).

Exemplary thienopyridines include clopidogrel and prasugrel. Clopidogrel (frequently prescribed in combination with aspirin) has been shown to be effective in reducing the rate of major adverse cardiovascular events following acute coronary syndrome and is a routine component of the clinical management of patients with this syndrome (Steinhubl, S R et al. (2002); Yusuf, S et al., (2001); Braunwald, E et al., (2002) and Smith S C, Jr et al. (2006). Clopidogrel is also prescribed to individuals receiving coronary stents during percutaneous coronary intervention to prevent early and late stent thrombosis.

Clopidogrel

Clopidogrel (IUPAC: (+)-(S)-methyl 2-(2-chlorophenyl)-2-(6,7-dihydrothieno[3,2-c]pyridin-5(4H)-yl)acetate), marketed as clopidogrel bisulfate under the trade names PLAVIX™ or ISCOVER™, is an oral antiplatelet agent widely prescribed in the treatment of diseases associated with platelet aggregation. Indeed, clopidogrel is reportedly the world's second highest selling pharmaceutical and the highest selling antiplatelet agent.

Clopidogrel bisulfate inhibits platelet aggregation by selectively and irreversibly inhibiting the binding of adenosine diphosphate (ADP) to its platelet receptor (the P2Y12 purinergic receptor) and the subsequent activation of ADP-mediated glycoprotein GPIIb/IIIa complex. Since this action is irreversible the remainder of the platelet lifespan is affected.

The bioavailability of the drug is approximately 50% and the drug is rapidly biotransformed in the liver to a short acting thiol ester. The thiol ester is the active component of the drug. Gut absorption and biotransformation in the liver are the rate limiting steps that most influence the efficacy of the drug. The p-glycoprotein drug efflux pump mechanism (ref) has been shown to influence the absorption of the drug and liver biotransformation is dependent on the activity of the cytochrome P450 enzyme system (CYP450). The principle cytochrome P450 enzymes responsible for biotransformation are outlined below. As the activity of the drug is dependent on these rate limiting steps peak effect is not seen until six hours after dosing.

The elimination half life of the drug is 7.2-7.6 hours and influenced by renal impairment which reduces parent drug excretion. A loading dose in individuals who have renal impairment or who are elderly is usually cautioned.

The following are FDA approved indications for clopidogrel:
  Acute coronary syndrome, Non-ST segment elevation—Thrombotic disorder; Prophylaxis
  Acute ST segment elevation myocardial infarction—Thrombotic disorder; Prophylaxis
  Arteriosclerotic vascular disease—Thrombotic disorder; Prophylaxis
  Cerebrovascular accident—Thrombotic disorder; Prophylaxis
  Myocardial infarction—Thrombotic disorder; Prophylaxis
  Peripheral arterial occlusive disease—Thrombotic disorder; Prophylaxis The following are current recommended dosing regimens for clopidogrel, however a loading dose of 600 mg is frequently prescribed in clinical practice:
  Acute coronary syndrome, Non-ST segment elevation—Thrombotic disorder; Prophylaxis: initial, 300 mg ORALLY once; with aspirin 75 mg to 325 mg ORALLY Acute coronary syndrome, Non-ST segment elevation—Thrombotic disorder; Prophylaxis: maintenance, 75 mg ORALLY once daily with aspirin 75 mg to 325 mg ORALLY once daily Acute ST segment elevation myocardial infarction—Thrombotic disorder; Prophylaxis: 300 mg ORALLY loading dose is optional; 75 mg ORALLY once daily in combination with aspirin, with or without thrombolytics;

Arteriosclerotic vascular disease—Thrombotic disorder; Prophylaxis: 75 mg ORALLY once daily Cerebrovascular accident—Thrombotic disorder; Prophylaxis: 75 mg ORALLY once daily Myocardial infarction—Thrombotic disorder; Prophylaxis: 75 mg ORALLY once daily Peripheral arterial occlusive disease—Thrombotic disorder; Prophylaxis: 75 mg ORALLY once daily Contraindications to clopidogrel include; bleeding, active (such as peptic ulcer or intracranial hemorrhage), hypersensitivity to clopidogrel or any component of the product. Precautions to clopdogrel are the combination of aspirin and clopidogrel in patients with recent TIA or stroke; which has been shown to increase major bleeding, elective surgery, severe liver disease, patients at risk of increased bleeding from trauma, surgery, or other pathological condition (particularly gastrointestinal and intraocular), premature discontinuation of therapy in percutaneous coronary intervention (PCI) patients; may increase risk of stent thrombosis, myocardial infarction, and death, renal impairment, severe thrombotic thrombocytopenic purpura, sometimes life-threatening, may occur, transbronchial lung biopsy; risk of bleeding greatly increased Prasugrel Prasugrel, Tradename EFFIENT™ (IUPAC: 5-[2-cyclopropyl-1-(2-fluorophenyl)-2-oxoethyl]-4,5,6,7-tetrahydrothieno[3,2-c]pyridin-2-yl acetate) is a novel third generation thienopyridine developed by Daiichi Sankyo Co. and produced by Ube and currently under clinical development in cooperation with Eli Lilly and Company for acute coronary syndromes planned for percutaneous coronary intervention (PCI). Studies comparing prasugrel to clopidogrel in healthy volunteers and patients with stable atherosclerosis have reported that prasugrel is more potent and achieves higher levels of inhibition of platelet aggregation (IPA) than seen with the approved 300 mg loading/75 mg maintenance dose regimen for clopidogrel (Asai, F, et al (2006); Jakubowski, J A et al (2006); Jernberg, T, et al (2006); Matsushima, N et al (2006) and Brandt, J T, Payne, C D et al (2007).

Prasugrel is rapidly absorbed and biotransformed into its active metabolite (R-138727) and the time to peak effect is approximately one hour. This has advantages to clopidogrel as time to onset of effect has been shown to correlate with clinical outcomes in the management of patients with acute coronary syndrome, receiving percutaneous coronary intervention.

The drug elimination half life is 3.7 hours and as the mechanism of action is similar to clopidogrel i.e. irreversibly inhibiting the binding of adenosine diphosphate (ADP) to its platelet receptor (the P2Y12 purinergic receptor) the duration of action is five to ten days which approximates the lifespan of a platelet.

The proposed pathways leading to conversion of prasugrel and clopidogrel to their respective active metabolites differ. Prasugrel is reportedly rapidly hydrolyzed in vivo by esterases to a thiolactone, and subsequently metabolized to the active metabolite in a single step by several CYP enzymes, mainly CYP3A4/5 and CYP2B6, and to a lesser extent by CYP2C19 and CYP2C9 (Rehmel et al (2006). In contrast, two sequential CYP-dependent oxidative steps are required to convert clopidogrel to its active metabolite. The first step leads to formation of 2-oxo-clopidogrel, which is then metabolized to the active metabolite. In a competing metabolic reaction, esterases convert clopidogrel to inactive metabolites; this inactivation pathway accounts for an estimated 85% of a dose of clopidogrel [28]. Enzymes involved in the metabolism of clopidogrel include CYP1A2, CYP2B6, CYP2C9, CYP2C19 and CYP3A4/5 [29-31].

Prasugrel is currently not approved for clinical use but an application for a new drug assessment (NDA) has been made. A number of clinical trials have now been published which have assessed the safety and efficacy of prasugrel. These are principally the JUMBO TIMI-26, TRITON TIMI-38 and PRINCIPLE-44 trial with the TRILOGY-TIMI trial ongoing. The JUMBO-TIMI trial found prasugrel to have a comparable safety profile to clopidogrel. However the recent TRITON TIMI-38 trial found that prasugrel reduced ischemic events in an acute coronary syndrome population undergoing PCI, at the cost of increased major bleeding. Those assigned to clopidogrel received a 300 mg loading dose immediately prior to or during PCI; whereas 600 mg is now more commonly-used clinically as it may be more effective. Although this raised the question of dose equivalence, platelet function analysis in PRINCIPLE-TIMI 44 has shown that the dose of prasugrel used in TRITON leads to greater platelet inhibition than clopidogrel at the higher loading and maintenance doses. Subgroup analysis of TRITON suggested prasugrel may have the greatest benefit over clopidogrel in the highest risk patients, such those with diabetes. Alternatively a possible future approach may be individualised antiplatelet therapy based on platelet function testing or pharmacogenetic profiling.

Pharmacogenetic testing may provide a cost effective means of administering this drug to those that will derive the most benefit i.e. those that are clopidogrel resistant. Alternatively pharmacogenetic testing may provide improved safety to patients as the overall number of bleeding events is likely to be reduced if a tailored strategy is adopted.

Other classes of antiplatelet agents include thrombin receptor antagonists and glycoprotein IIb/IIIa inhibitors. These agents may also be preferable in individuals who are nonresponders to clopidogrel. A thrombin receptor (also known as protease-activated receptor-1 (PAR-1)) antagonist is entering a Phase III trial and may be available for clinical use in the near future. Thrombin is the most potent agonist of platelet activation and despite the current blockade of antiplatelet pathways with aspirin and clopidogrel persistent thrombin generation poses a considerable continued stimulus for platelets. Blocking this particular platelet PAR-1 receptor leaves other thrombin-mediated haemostatic functions intact, so theoretically bleeding events may not be increased.

The glycoprotein IIb/IIIa inhibitors are considered the most potent antiplatelet agents as they inhibit the final common pathway of platelet aggregation. However they do not mitigate the upstream effects of platelet activation that result in the release of vasoactive substances in high-risk PCI patients. Clinical trials suggest that combination therapy of glycoprotein IIb/IIIa inhibitors and P2Y12 receptor antagonists may reduce preprocedural myonecrosis and improve long-term ischemic outcomes, compared with either drug alone.

Platelet Function

Traditional methods of platelet function testing are complicated to perform, requiring skilled and experienced phlebotomy and laboratory staff working under carefully controlled conditions. Laboratory-based LTA is accepted by most as the "gold standard", but is labour intensive, operator-dependent and expensive, which has restricted its clinical use (Harrison P (2005)). These limitations have led investigators to use surrogates for platelet function including biochemical markers such as serum or urine thromboxane B2 for aspirin activity, and vasodilator-stimulated phosphoprotein (VASP) for P2Y12 receptor inhibition (Table 1) (Eikelbroom J W et al., (2002) and Geiger J et al., (1999)).

specific cartridges that test for the effects of aspirin, clopidogrel and GpIIbIIIa inhibitors, all validated against light transmittance aggregometry (van Werkum J W et al., (2006), Coleman J L W J and Simon D I (2004), Wheeler G L et al., (2002)).

These devices test a single pathway of platelet activation (Gurbel P A, Bliden K P, Di Chiara J et al., (2007). A study of 700 patients found that residual arachidonic acid-induced platelet aggregation in patients on aspirin was due to ADP-

TABLE 1

Exemplary Platelet Function Analysers and Clinical Correlates

| Platelet Function analyser | Advantages | Disadvantages | Clinical Outcome Studies | Monitors ASA and Clopidogrel |
|---|---|---|---|---|
| Bleeding time* | Widely available, in vivo | highly variable, non-specific activation, scarring | No | No |
| PFA-100* | Rapid, whole blood, hypothesised to mimic small vessel, measures shear stress effect | Requires pipetting of blood, inter-instrument variability, non-continuous output, dependent on vWF levels | Yes | No |
| VerifyNow* | Closed system, rapid, correlates with gold standard, small footprint | Older model influenced by ambient light | Yes | Yes |
| Thromboelastogram (TEG)* | Small footprint, has advantages for cardiac anaesthetists | Requires pipetting of blood (operator dependent results), difficult to interpret output variables, minimal clinical studies | Yes | Yes with platelet mapping |
| Light transmittance aggregometry | Historic gold standard | Operator dependent, requires preparation of plasma and pipetting, costly, time consuming | Yes | Yes |
| Urinary 11-dehydro-thromboxane B2 | Specific to COX-1 activity | Not specific to platelet COX-1, dependent on renal function and urinary concentration | Yes | No |
| VASP | Specific to P2Y12 activity | Expensive, requires flow cytometer, technical experience required | Yes | No |

PFA = Platelet function analyser, COX = Cyclo-oxygenase, VASP = Vasodilator stimulated phosphoprotein. Other platelet function measures include CD40L, P-Selectin, and platelet derived microparticles.
*denotes point-of-care assay Platelet function assays can be classified according to the method of analysis. Biochemical assays utilise either an ELISA assay (thromboxane) or flow cytometry (VASP). Non-biochemical platelet function analysers typically use light transmittance or electrical impedance to measure platelet aggregation directly, either in isolated platelets or in whole blood (Dyszkiewicz-Korpanty A M et al., (2005)). The platelet agonist may differ between assays, making inter-assay comparisons difficult. Few analysers incorporate increased shear stress as a non-biochemical means of platelet stimulation (Schlammadinger A et al., (2000)).

Point-of-care platelet function devices have simplified testing with a rapid result available at the bedside or in the cardiac catheterisation laboratory. The three most widely-evaluated point-of-care devices are Dade-Behring's PFA-100™, which measures platelet function under high shear stress by drawing blood through a small aperture and measuring the "closure time" of that aperture by a platelet plug, Accumetric's VerifyNow™ assay which uses a light-based, whole blood aggregometry system, and the Thromboelastograph (TEG™), which measures clot tensile strength and has been most widely evaluated and used in patients undergoing cardiac surgery.

The PFA-100 has been used clinically in the diagnosis of platelet function disorders (Hayward C P et al., (2006). Its cartridges have collagen and either arachidonic acid or ADP as the agonist. The VerifyNow™ device has three pathway-dependent rather than cyclo-oxygenase pathways (Frielinger A L et al., (2006). The authors concluded that "aspirin resistance", as measured by a point-of-care platelet function analyzer specific to aspirin, is either a limitation of the device due to pathway nonspecificity or simply a measure of non-compliance with aspirin (Frielinger A L et al., (2006). This hypothesis is supported by the recent ASPECT study, a comprehensive assessment of a range of platelet function analysers, which concluded that aspirin non-responsiveness is rare, overcalled by some analysers like the PFA-100, and may be related to non COX-1 pathways such as those mediated by ADP (Gurbel P A, Bliden K P, Di Chiara J et al., (2007).

It will therefore be apparent that while a number of assays for platelet function (including platelet inhibition) exist, those more suitable for use in the present invention are able to be performed rapidly, and preferably involve the use of a point-of-care device for rapid assessment.

Reference herein to a percentage platelet inhibition, for example 10% platelet inhibition, refers to platelet inhibition measured by the VerifyNow device. It will be apparent that % platelet inhibition derived by other assay methods or devices can be converted to, expressed relative to, or referenced to such % platelet inhibition. Methods to determine equivalence between platelet function assays are well known in the art.

Acute Coronary Syndrome

Acute coronary syndrome ("ACS") is a complex disorder which has been variously defined. See, for example, U.S. Pat.

No. 6,706,689, wherein ACS denotes subjects who have or are at high risk of developing an acute myocardial infarction (MI), and includes unstable angina (UA), non-Q-wave cardiac necrosis (NQCN) and Q-wave MI (QMI). As described therein, ACS is typically diagnosed when a patient has acute (i.e., sudden onset) chest pain of a cardiac origin that is either new or clearly different from pre-existing, chronic, stable angina; that is, ACS chest pain is more severe, more frequent, occurs at rest, or is longer than 15 minutes in duration. After ACS has been diagnosed, the patient is stratified into UA, NQCN, and QMI, using criteria set forth in U.S. Pat. No. 6,706,689. As described therein, Q-wave MI generally is understood to result from total occlusion of a coronary artery, whereas UA is caused by a subtotal occlusion. Again as described in U.S. Pat. No. 6,706,689, a number of clinical indicators that aid a diagnosis of ACS are known including elevated troponin 1 levels, elevated troponin T levels, elevated CK-MB levels, and elevated LDH, LDH1 and LDH2 levels. Newer definitions of MI categorise individuals into groups depending on ST segment analysis of the cardiac electrocardiogram (ECG) and troponin. Thereby UA, NQCN and QMI are now considered non-ST elevation (NSTE) MI if the ST segment is either normal or depressed. An ST elevation MI is diagnosed if the ST segment is elevated at the J point in two contiguous ECG leads with the cut-off points $\geq 0.2$ mV in men or $\geq 0.15$ mV in women in leads V2-3 and/or $\geq 0.1$ mV in other leads. In the new universal definition of MI, published in the European Heart Journal 2007, troponin elevation of any kind is defined as myocardial necrosis i.e. infarction.

Local and systemic inflammatory processes, including pro-inflammatory cytokine generation and release and localisation and activation of inflammatory cells including foam cells, macrophages, lymphocytes, and mast cells are associated with arterial inflammation and have been implicated in the pathogenesis of ACS (See Mulvihill N T and Foley J B, 2001), and are believed to play a significant pathophysiologic role in coronary plaque disruption. Plaque disruption in turn leads to inter alia platelet aggregation and thrombosis. It is recognised that thrombosis underlies most acute complications of atherosclerosis, notably unstable angina and acute myocardial infarction.

Accordingly, as used herein ACS includes arterial inflammation and ACS-associated impaired vascular function, which may be evident before diagnosable ACS is evident. As used herein, the phrase "ACS-associated impaired vascular function" contemplates ischemia, vasoconstriction, coronary spasm, erosion, occlusion, plaque rupture, impaired platelet aggregation, and the like. Although it perhaps represents ACS-associated impaired vascular function in extremis, thrombosis per se will typically be considered evidentiary of ACS, rather than impaired vascular function.

It will be apparent that polymorphisms in linkage disequilibrium with one or more other polymorphism associated with increased or decreased response to an antiplatelet agent will also provide utility as biomarkers for response to an antiplatelet agent. The frequency for SNPs in linkage disequilibrium are often very similar. Accordingly, these genetically linked SNPs can be utilized in combined polymorphism analyses to derive a level of risk comparable to that calculated from the original SNP.

It will therefore be apparent that one or more polymorphisms in linkage disequilibrium with the polymorphisms specified herein can be identified, for example, using public data bases.

It will also be apparent that frequently a variety of nomenclatures may exist for any given polymorphism. When referring to a resistance or responsive polymorphism as herein described, alternative nomenclatures are also contemplated by the present invention. Generally, such alternative nomenclatures can be readily identified by investigating for example the Genbank database using the unique identifier (e.g., the rs number) for a particular SNP.

Identification and Analysis of Polymorphisms

It will be understood that in the context of the present invention the term "polymorphism" means the occurrence together in the same population at a rate greater than that attributable to random mutation (usually greater than 1%) of two or more alternate forms (such as alleles or genetic markers) of a chromosomal locus that differ in nucleotide sequence or have variable numbers of repeated nucleotide units. See www.ornl.gov/sci/techresources/Human_Genome/publicat/97pr/09gloss.html#p. Accordingly, the term "polymorphisms" is used herein contemplates genetic variations, including single nucleotide substitutions, insertions and deletions of nucleotides, repetitive sequences (such as microsatellites), and the total or partial absence of genes (eg. null mutations). As used herein, the term "polymorphisms" also includes genotypes and haplotypes. A genotype is the genetic composition at a specific locus or set of loci. A haplotype is a set of closely linked genetic markers present on one chromosome which are not easily separable by recombination, tend to be inherited together, and may be in linkage disequilibrium. A haplotype can be identified by patterns of polymorphisms such as SNPs. Similarly, the term "single nucleotide polymorphism" or "SNP" in the context of the present invention includes single base nucleotide substitutions and short deletion and insertion polymorphisms.

The methods of the invention are primarily directed to the detection and identification of the above polymorphisms associated with response to an antiplatelet agent, preferably clopidogrel. These polymorphisms are typically single nucleotide polymorphisms. In general terms, a single nucleotide polymorphism (SNP) is a single base change or point mutation resulting in genetic variation between individuals. SNPs occur in the human genome approximately once every 100 to 300 bases, and can occur in coding or non-coding regions. Due to the redundancy of the genetic code, a SNP in the coding region may or may not change the amino acid sequence of a protein product. A SNP in a non-coding region can, for example, alter gene expression by, for example, modifying control regions such as promoters, transcription factor binding sites, processing sites, ribosomal binding sites, and affect gene transcription, processing, and translation.

SNPs can facilitate large-scale association genetics studies, and there has recently been great interest in SNP discovery and detection. SNPs show great promise as markers for a number of phenotypic traits (including latent traits), such as for example, disease propensity and severity, wellness propensity, and drug responsiveness including, for example, susceptibility to adverse drug reactions. Knowledge of the association of a particular SNP with a phenotypic trait, coupled with the knowledge of whether an individual has said particular SNP, can enable the targeting of diagnostic, preventative and therapeutic applications to allow better disease management, to enhance understanding of disease states and to ultimately facilitate the discovery of more effective treatments, such as personalised treatment regimens.

Indeed, a number of databases have been constructed of known SNPs, and for some such SNPs, the biological effect associated with a SNP. For example, the NCBI SNP database "dbSNP" is incorporated into NCBI's Entrez system and can be queried using the same approach as the other Entrez databases such as PubMed and GenBank. This database has records for over 1.5 million SNPs mapped onto the human genome sequence. Each dbSNP entry includes the sequence context of the polymorphism (i.e., the surrounding sequence), the occurrence frequency of the polymorphism (by population or individual), and the experimental method(s), protocols, and conditions used to assay the variation, and can include information associating a SNP with a particular phenotypic trait.

At least in part because of the potential impact on health and wellness, there has been and continues to be a great deal of effort to develop methods that reliably and rapidly identify SNPs. This is no trivial task, at least in part because of the complexity of human genomic DNA, with a haploid genome of $3 \times 10^9$ base pairs, and the associated sensitivity and discriminatory requirements.

Genotyping approaches to detect SNPs well-known in the art include DNA sequencing, methods that require allele specific hybridization of primers or probes, allele specific incorporation of nucleotides to primers bound close to or adjacent to the polymorphisms (often referred to as "single base extension", or "minisequencing"), allele-specific ligation (joining) of oligonucleotides (ligation chain reaction or ligation padlock probes), allele-specific cleavage of oligonucleotides or PCR products by restriction enzymes (restriction fragment length polymorphisms analysis or RFLP) or chemical or other agents, resolution of allele-dependent differences in electrophoretic or chromatographic mobilities, by structure specific enzymes including invasive structure specific enzymes, or mass spectrometry. Analysis of amino acid variation is also possible where the SNP lies in a coding region and results in an amino acid change.

DNA sequencing allows the direct determination and identification of SNPs. The benefits in specificity and accuracy are generally outweighed for screening purposes by the difficulties inherent in whole genome, or even targeted subgenome, sequencing.

Mini-sequencing involves allowing a primer to hybridize to the DNA sequence adjacent to the SNP site on the test sample under investigation. The primer is extended by one nucleotide using all four differentially tagged fluorescent dideoxynucleotides (A, C, G, or T), and a DNA polymerase. Only one of the four nucleotides (homozygous case) or two of the four nucleotides (heterozygous case) is incorporated. The base that is incorporated is complementary to the nucleotide at the SNP position.

A number of methods currently used for SNP detection involve site-specific and/or allele-specific hybridisation. These methods are largely reliant on the discriminatory binding of oligonucleotides to target sequences containing the SNP of interest. The techniques of Affymetrix (Santa Clara, Calif.) and Nanogen Inc. (San Diego, Calif.) are particularly well-known, and utilize the fact that DNA duplexes containing single base mismatches are much less stable than duplexes that are perfectly base-paired. The presence of a matched duplex is detected by fluorescence.

The majority of methods to detect or identify SNPs by site-specific hybridisation require target amplification by methods such as PCR to increase sensitivity and specificity (see, for example U.S. Pat. No. 5,679,524, PCT publication WO 98/59066, PCT publication WO 95/12607). US Application 20050059030 (incorporated herein in its entirety) describes a method for detecting a single nucleotide polymorphism in total human DNA without prior amplification or complexity reduction to selectively enrich for the target sequence, and without the aid of any enzymatic reaction. The method utilises a single-step hybridization involving two hybridization events: hybridization of a first portion of the target sequence to a capture probe, and hybridization of a second portion of said target sequence to a detection probe. Both hybridization events happen in the same reaction, and the order in which hybridisation occurs is not critical.

US Publication 20050042608 (incorporated herein in its entirety) describes a modification of the method of electrochemical detection of nucleic acid hybridization of Thorp et al. (U.S. Pat. No. 5,871,918). Briefly, capture probes are designed, each of which has a different SNP base and a sequence of probe bases on each side of the SNP base. The probe bases are complementary to the corresponding target sequence adjacent to the SNP site. Each capture probe is immobilized on a different electrode having a non-conductive outer layer on a conductive working surface of a substrate. The extent of hybridization between each capture probe and the nucleic acid target is detected by detecting the oxidation-reduction reaction at each electrode, utilizing a transition metal complex. These differences in the oxidation rates at the different electrodes are used to determine whether the selected nucleic acid target has a single nucleotide polymorphism at the selected SNP site.

The technique of Lynx Therapeutics (Hayward, Calif.) using MEGATYPE™ technology can genotype very large numbers of SNPs simultaneously from small or large pools of genomic material. This technology uses fluorescently labeled probes and compares the collected genomes of two populations, enabling detection and recovery of DNA fragments spanning SNPs that distinguish the two populations, without requiring prior SNP mapping or knowledge.

A number of other methods for detecting and identifying SNPs exist. These include the use of mass spectrometry, for example, to measure probes that hybridize to the SNP. This technique varies in how rapidly it can be performed, from a few samples per day to a high throughput of 40,000 SNPs per day, using mass code tags. A preferred example is the use of mass spectrometric determination of a nucleic acid sequence which comprises the polymorphisms of the invention, for example, which includes the promoter of the COX2 gene or a complementary sequence. Such mass spectrometric methods are known to those skilled in the art, and the genotyping methods of the invention are amenable to adaptation for the mass spectrometric detection of the polymorphisms of the invention, for example, the COX2 promoter polymorphisms of the invention.

SNPs can also be determined by ligation-bit analysis. This analysis requires two primers that hybridize to a target with a one nucleotide gap between the primers. Each of the four nucleotides is added to a separate reaction mixture containing DNA polymerase, ligase, target DNA and the primers. The polymerase adds a nucleotide to the 3' end of the first primer that is complementary to the SNP, and the ligase then ligates the two adjacent primers together. Upon heating of the sample, if ligation has occurred, the now larger primer will remain hybridized and a signal, for example, fluorescence, can be detected. A further discussion of these methods can be found in U.S. Pat. Nos. 5,919,626; 5,945,283; 5,242,794; and 5,952,174.

U.S. Pat. No. 6,821,733 (incorporated herein in its entirety) describes methods to detect differences in the sequence of two nucleic acid molecules that includes the steps of: contacting two nucleic acids under conditions that allow the formation of a four-way complex and branch migration; contacting the four-way complex with a tracer molecule and a detection molecule under conditions in which the detection molecule is capable of binding the tracer molecule or the four-way complex; and determining binding of the tracer molecule to the detection molecule before and after exposure to the four-way complex. Competition of the four-way complex with the tracer molecule for binding to the detection molecule indicates a difference between the two nucleic acids.

Protein- and proteomics-based approaches are also suitable for polymorphism detection and analysis. Polymorphisms which result in or are associated with variation in expressed proteins can be detected directly by analysing said proteins. This typically requires separation of the various proteins within a sample, by, for example, gel electrophoresis or HPLC, and identification of said proteins or peptides derived therefrom, for example by NMR or protein sequencing such as chemical sequencing or more prevalently mass spectrometry. Proteomic methodologies are well known in the art, and have great potential for automation. For example, integrated systems, such as the ProteomIQ™ system from Proteome Systems, provide high throughput platforms for proteome analysis combining sample preparation, protein separation, image acquisition and analysis, protein processing, mass spectrometry and bioinformatics technologies.

The majority of proteomic methods of protein identification utilise mass spectrometry, including ion trap mass spectrometry, liquid chromatography (LC) and LC/MSn mass spectrometry, gas chromatography (GC) mass spectroscopy, Fourier transform-ion cyclotron resonance-mass spectrometer (FT-MS), MALDI-TOF mass spectrometry, and ESI mass spectrometry, and their derivatives. Mass spectrometric methods are also useful in the determination of post-translational modification of proteins, such as phosphorylation or glycosylation, and thus have utility in determining polymorphisms that result in or are associated with variation in post-translational modifications of proteins.

Associated technologies are also well known, and include, for example, protein processing devices such as the "Chemical Inkjet Printer" comprising piezoelectric printing technology that allows in situ enzymatic or chemical digestion of protein samples electroblotted from 2-D PAGE gels to membranes by jetting the enzyme or chemical directly onto the selected protein spots. After in-situ digestion and incubation of the proteins, the membrane can be placed directly into the mass spectrometer for peptide analysis.

A large number of methods reliant on the conformational variability of nucleic acids have been developed to detect SNPs.

For example, Single Strand Conformational Polymorphism (SSCP, Orita et al., PNAS 1989 86:2766-2770) is a method reliant on the ability of single-stranded nucleic acids to form secondary structure in solution under certain conditions. The secondary structure depends on the base composition and can be altered by a single nucleotide substitution, causing differences in electrophoretic mobility under nondenaturing conditions. The various polymorphs are typically detected by autoradiography when radioactively labelled, by silver staining of bands, by hybridisation with detectably labelled probe fragments or the use of fluorescent PCR primers which are subsequently detected, for example by an automated DNA sequencer.

Modifications of SSCP are well known in the art, and include the use of differing gel running conditions, such as for example differing temperature, or the addition of additives, and different gel matrices. Other variations on SSCP are well known to the skilled artisan, including, RNA-SSCP, restriction endonuclease fingerprinting-SSCP, dideoxy fingerprinting (a hybrid between dideoxy sequencing and SSCP), bi-directional dideoxy fingerprinting (in which the dideoxy termination reaction is performed simultaneously with two opposing primers), and Fluorescent PCR-SSCP (in which PCR products are internally labelled with multiple fluorescent dyes, may be digested with restriction enzymes, followed by SSCP, and analysed on an automated DNA sequencer able to detect the fluorescent dyes).

Other methods which utilise the varying mobility of different nucleic acid structures include Denaturing Gradient Gel Electrophoresis (DGGE), Temperature Gradient Gel Electrophoresis (TGGE), and Heteroduplex Analysis (HET). Here, variation in the dissociation of double stranded DNA (for example, due to base-pair mismatches) results in a change in electrophoretic mobility. These mobility shifts are used to detect nucleotide variations.

Denaturing High Pressure Liquid Chromatography (HPLC) is yet a further method utilised to detect SNPs, using HPLC methods well-known in the art as an alternative to the separation methods described above (such as gel electrophoresis) to detect, for example, homoduplexes and heteroduplexes which elute from the HPLC column at different rates, thereby enabling detection of mismatch nucleotides and thus SNPs.

Yet further methods to detect SNPs rely on the differing susceptibility of single stranded and double stranded nucleic acids to cleavage by various agents, including chemical cleavage agents and nucleolytic enzymes. For example, cleavage of mismatches within RNA:DNA heteroduplexes by RNase A, of heteroduplexes by, for example bacteriophage T4 endonuclease YII or T7 endonuclease I, of the 5' end of the hairpin loops at the junction between single stranded and double stranded DNA by cleavase I, and the modification of mispaired nucleotides within heteroduplexes by chemical agents commonly used in Maxam-Gilbert sequencing chemistry, are all well known in the art.

Further examples include the Protein Translation Test (PTT), used to resolve stop codons generated by variations which lead to a premature termination of translation and to protein products of reduced size, and the use of mismatch binding proteins. Variations are detected by binding of, for example, the MutS protein, a component of *Escherichia coli* DNA mismatch repair system, or the human hMSH2 and GTBP proteins, to double stranded DNA heteroduplexes containing mismatched bases. DNA duplexes are then incubated with the mismatch binding protein, and variations are detected by mobility shift assay. For example, a simple assay is based on the fact that the binding of the mismatch binding protein to the heteroduplex protects the heteroduplex from exonuclease degradation.

Those skilled in the art will know that a particular SNP, particularly when it occurs in a regulatory region of a gene such as a promoter, can be associated with altered expression of a gene. Altered expression of a gene can also result when the SNP is located in the coding region of a protein-encoding gene, for example where the SNP is associated with codons of varying usage and thus with tRNAs of differing abundance. Such altered expression can be determined by methods well known in the art, and can thereby be employed to detect such SNPs. Similarly, where a SNP occurs in the coding region of a gene and results in a non-synonomous amino acid substitution, such substitution can result in a change in the function of the gene product. Similarly, in cases where the gene product is an RNA, such SNPs can result in a change of function in the RNA gene product. Any such change in function, for example as assessed in an activity or functionality assay, can be employed to detect such SNPs.

The above methods of detecting and identifying SNPs are amenable to use in the methods of the invention.

Of course, in order to detect and identify SNPs in accordance with the invention, a sample containing material to be tested is obtained from the subject. The sample can be any sample potentially containing the target SNPs (or target polypeptides, as the case may be) and obtained from any bodily fluid (blood, urine, saliva, etc) biopsies or other tissue preparations.

DNA or RNA can be isolated from the sample according to any of a number of methods well known in the art. For example, methods of purification of nucleic acids are described in Tijssen; Laboratory Techniques in Biochemistry and Molecular Biology: Hybridization with nucleic acid probes Part 1: Theory and Nucleic acid preparation, Elsevier, New York, N.Y. 1993, as well as in Maniatis, T., Fritsch, E. F. and Sambrook, J., Molecular Cloning Manual 1989.

To assist with detecting the presence or absence of polymorphisms/SNPs, nucleic acid probes and/or primers can be provided. Such probes and/or primers have nucleic acid sequences specific for chromosomal changes evidencing the presence or absence of the polymorphism and are preferably labeled with a substance that emits a detectable signal when combined with the target polymorphism.

The nucleic acid probes and/or primers can be genomic DNA or cDNA or mRNA, or any RNA-like or DNA-like material, such as peptide nucleic acids, branched DNAs, and the like. The probes can be sense or antisense polynucleotide probes. Where target polynucleotides are double-stranded, the probes may be either sense or antisense strands. Where the target polynucleotides are single-stranded, the probes are complementary single strands.

The probes and/or primers can be prepared by a variety of synthetic or enzymatic schemes, which are well known in the art. The probes and/or primers can be synthesized, in whole or in part, using chemical methods well known in the art (Caruthers et al., *Nucleic Acids Res., Symp. Ser.,* 215-233 (1980)). Alternatively, the probes can be generated, in whole or in part, enzymatically.

Nucleotide analogs can be incorporated into probes and/or primers by methods well known in the art. The only requirement is that the incorporated nucleotide analog must serve to base pair with target polynucleotide sequences. For example, certain guanine nucleotides can be substituted with hypoxanthine, which base pairs with cytosine residues. However, these base pairs are less stable than those between guanine and cytosine. Alternatively, adenine nucleotides can be substituted with 2,6-diaminopurine, which can form stronger base pairs than those between adenine and thymidine.

Additionally, the probes and/or primers can include nucleotides that have been derivatized chemically or enzymatically. Typical chemical modifications include derivatization with acyl, alkyl, aryl or amino groups.

The probes can be immobilized on a substrate. Preferred substrates are any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which the polynucleotide probes are bound. Preferably, the substrates are optically transparent.

Furthermore, the probes do not have to be directly bound to the substrate, but rather can be bound to the substrate through a linker group. The linker groups are typically about 6 to 50 atoms long to provide exposure to the attached probe. Preferred linker groups include ethylene glycol oligomers, diamines, diacids and the like. Reactive groups on the substrate surface react with one of the terminal portions of the linker to bind the linker to the substrate. The other terminal portion of the linker is then functionalized for binding the probe.

The probes can be attached to a substrate by dispensing reagents for probe synthesis on the substrate surface or by dispensing preformed DNA fragments or clones on the substrate surface. Typical dispensers include a micropipette delivering solution to the substrate with a robotic system to control the position of the micropipette with respect to the substrate. There can be a multiplicity of dispensers so that reagents can be delivered to the reaction regions simultaneously.

Nucleic acid primers suitable for detecting the presence or absence of polymorphisms may be designed and synthesised by methods well known in the art. For example, primers suitable for primer extension and/or sequencing may be designed to bind immediately upstream of the polymorphic site, so that when extended the identity of the nucleotide at the polymorphic site is determined. Such primers are exemplary of primers that are able to be used to span the polymorphic region of the genes described herein. Those skilled in the art will appreciate that appropriate primer sequences may be derived from the sequence upstream or downstream of the polymorphic site, such as that presented in the ENTREZ database entry for each SNP (by reference to the unique identifier, or RS number). For example, as described herein in the Examples, genotyping of individuals may be readily performed using mass spectrometry. This is generally performed utilising primer extension of primers derived from "context sequences" (see, for example, www.appliedbiosystems.com). Exemplary context sequences suitable for use in designing primers suitable for use in the present invention include:

ATGTGGTCCAAACAGGGAAGAGATA[T/C]TGAAAGACAAAAGAGCTCTTTAAAG [SEQ ID No. 1] (for the 6986G/A (rs776746) polymorphism in the gene encoding CYP3A5)

GTCTTAACAAGAGGAGAAGGCTTCA[A/G]TGGATCCTTTTGTGGTCCTTGTGCT [SEQ ID No. 2] (for the 1A/G (rs28399504) polymorphism in the gene encoding CYP2C19);

AAATTTGTGTCTTCTGTTCTCAAAG[C/T]ATCTCTGATGTAAGAGATAATGCGC [SEQ ID No. 3] (for the −806C/T (rs12248560) polymorphism in the gene encoding CYP2C19;

ACGTCTCAGGGCCTCAGCTTGACCT[A/G]TCCCCCAGGTTCAGAGTGTGGGCTG [SEQ ID No. 4] (for the 275A/G (rs1464602) polymorphism in the gene encoding NR1I2);

TTCCCACTATCATTGATTATTTCCC[A/G]GGAACCCATAACAAATTACTTAAAA [SEQ ID No. 5] (for the 19154G/A (rs4244285) polymorphism in the gene encoding CYP2C19); and TGTGGTGCACGAGGTCCAGAGATAC[C/A]TTGACCTTCTCCCCACCAGCCTGCC [SEQ ID No. 6] (for the 42614A/C (rs1057910) polymorphism in the gene encoding CYP2C9).

ACATCAGGATTGTAAGCACCCCCTG[A/G]ATCCAGGTAAGGCCAAGTTTTTTGC [SEQ ID No. 7] (for the 636G>A (rs4986893) polymorphism in the gene encoding CYP2C19).

CACCTTCCTCTTCCA[G/T]TCCATTACCGCCAAC [SEQ ID No. 8] (for the 516G>T (rs3745274) polymorphism in the gene encoding CYP2B6).

By way of example, primers suitable for detection of the 636G>A (rs4986893) polymorphism in the gene encoding CYP2C19 in a PCR method or similar include as upstream primer TGAAAACATCAGGATTGTAAGCACCCCCTG [SEQ ID NO:9], or as downstream primer ATCCAGGTAAGGCCAAGTTTTTTGCTTCCT [SEQ ID NO:10].

Likewise, primers suitable for detection of the rs3745274 polymorphism in the gene encoding CYP2B6 in a PCR method or similar include as upstream primer GGCCCT-CATGGACCCCACCTTCCTCTTCCA [SEQ ID NO:11], or as downstream primer TCCATTACCGCCAACATCATCT-GCTCCATC [SEQ ID NO:12].

Primers suitable for use in other detection methods well known in the art, for example PCR, TAQMAN, RTPCR and the like, are also contemplated.

Nucleic acid microarrays are preferred. Such microarrays (including nucleic acid chips) are well known in the art (see, for example U.S. Pat. Nos. 5,578,832; 5,861,242; 6,183,698; 6,287,850; 6,291,183; 6,297,018; 6,306,643; and 6,308,170, each incorporated by reference). Genotyping platforms well known in the art are U.S. Pat. Nos. 7,110,585; 7,354,389.

Alternatively, antibody microarrays can be produced. The production of such microarrays is essentially as described in Schweitzer & Kingsmore, "Measuring proteins on microarrays", *Curr Opin Biotechnol* 2002; 13(1): 14-9; Avseekno et al., "Immobilization of proteins in immunochemical microarrays fabricated by electrospray deposition", *Anal Chem* 2001 15; 73(24): 6047-52; Huang, "Detection of multiple proteins in an antibody-based protein microarray system, *Immunol Methods* 2001 1; 255 (1-2): 1-13.

The present invention also contemplates the preparation of kits for use in accordance with the present invention. Suitable kits include various reagents for use in accordance with the present invention in suitable containers and packaging materials, including tubes, vials, and shrink-wrapped and blow-molded packages.

Materials suitable for inclusion in an exemplary kit in accordance with the present invention comprise one or more of the following: gene specific PCR primer pairs (oligonucleotides) that anneal to DNA or cDNA sequence domains that flank the genetic polymorphisms of interest, reagents capable of amplifying a specific sequence domain in either genomic DNA or cDNA without the requirement of performing PCR; reagents required to discriminate between the various possible alleles in the sequence domains amplified by PCR or non-PCR amplification (e.g., restriction endonucleases, oligonucleotide that anneal preferentially to one allele of the polymorphism, including those modified to contain enzymes or fluorescent chemical groups that amplify the signal from the oligonucleotide and make discrimination of alleles more robust); reagents required to physically separate products derived from the various alleles (e.g. agarose or polyacrylamide and a buffer to be used in electrophoresis, HPLC columns, SSCP gels, formamide gels or a matrix support for MALDI-TOF).

It will be appreciated that the methods of the invention can be performed in conjunction with an analysis of other non-genetic factors known to be associated with a subject's likely response to an antiplatelet agent. Such factors include epidemiological risk factors associated with poor response or resistance to an antiplatelet agent. Such risk factors include, but are not limited to smoking and/or exposure to tobacco smoke, age, sex and familial history. These risk factors can be used to augment an analysis of one or more polymorphisms as herein described when assessing a subject's response to an antiplatelet agent.

It is recognised that individual SNPs may confer weak risk of susceptibility or protection to a disease or phenotype of interest. These modest effects from individual SNPs are typically measured as odds ratios in the order of 1-3. The specific phenotype of interest may be a disease, such as a disease or condition associated with platelet aggregation, or impaired drug response, or an intermediate phenotype based on a pathological, biochemical or physiological abnormality (for example, variant ADP receptor). As described herein, the effect of more than one responsive or restrictive polymorphisms can be combined to more accurately predict or determine a subject's response to an antiplatelet agent, or their suitability to a treatment regime.

In addition to identifying responsive or unresponsive individuals based on their combined genetic score, it is possible to segment a population to define a subgroup of the population that is suitable to undergo an intervention. Such an intervention may be a diagnostic intervention, such as imaging test, other screening or diagnostic test (eg biochemical or RNA based test), or may be a therapeutic intervention, such as a chemopreventive or chemotherapeutic therapy, or a preventive lifestyle modification (such as stopping smoking or increasing exercise). In defining such a clinical threshold, people can be prioritised to a particular intervention in such a way to minimise costs or minimise risks of that intervention (for example, the costs of image-based screening or expensive preventive treatment or risk from drug side-effects or risk from radiation exposure). In determining this threshold, one might aim to maximise the ability of the test to detect the majority of cases (maximise sensitivity) but also to minimise the number of people at low risk that require, or may be are otherwise eligible for, the intervention of interest.

Receiver-operator curve (ROC) analyses analyse the clinical performance of a test by examining the relationship between sensitivity and false positive rate (i.e., 1-specificity) for a single variable in a given population. In an ROC analysis, the test variable may be derived from combining several factors. An exemplary ROC analysis used to analyse a combined genetic score is presented herein Accordingly, the present invention also provides a method of assessing a subject's suitability for an intervention diagnostic of or therapeutic for a disease or condition associated with platelet aggregation, the method comprising:
  a) providing the result of one or more genetic tests of a sample from the subject, and
  b) analysing the result for the presence or absence of one or more responsive polymorphisms or for the presence or absence of one or more resistance polymorphisms, wherein said responsive or resistance polymorphisms are selected from the group consisting of:
6986G/A (rs776746) in the gene encoding CYP3A5; 31611T/C in the gene encoding CYP3A5; 1A/G (rs28399504) in the gene encoding CYP2C19; 636 G>A (rs4986893) in the gene encoding CYP2C19; −806C/T (rs12248560) in the gene encoding CYP2C19; 275A/G (rs1464602) in the gene encoding NR1I2; or one or more polymorphisms which are in linkage disequilibrium with any one or more of said polymorphisms;
  wherein the presence of one or more responsive polymorphisms is indicative of the subject's suitability for the intervention, and wherein the absence of one or more responsive polymorphisms or the presence of one or more resistance polymorphisms is indicative of the subject's unsuitability for the intervention.

The intervention may be a diagnostic test for the disease, such as a blood test or a CT scan for ACS. Alternatively, the intervention may be a therapy for the disease, such as chemotherapy or radiotherapy, including a preventative therapy for the disease, such as the provision of motivation to the subject to stop smoking.

The implementation of the methods of the invention in computer systems and programs as described herein, the data produced by such methods, and the use of such data in the prediction or determination of a subject's response to an antiplatelet agent, or in the determination of a subject's suitability or unsuitability for an intervention diagnostic or therapeutic of a disease or condition associated with platelet aggregation are also contemplated.

As used herein, the phrase "assessing a subject's suitability for an intervention" or grammatical equivalents thereof means one or more determinations of whether a given subject is or should be a candidate for an intervention or is not or should not be a candidate for an intervention. Preferably, the assessment involves a determination of the subject's SNP score in relation to a distribution of SNP scores as described herein.

As used herein the term "intervention" includes medical tests, analyses, and treatments, including diagnostic, therapeutic and preventative treatments, and psychological or psychiatric tests, analyses and treatments, including counseling and the like.

Computer-Related Embodiments

It will also be appreciated that the methods of the invention are amenable to use with and the results analysed by computer systems, software and processes. Computer systems, software and processes to identify and analyse genetic polymorphisms are well known in the art. Similarly, implementation of the algorithm utilised to generate a SNP score as described herein in computer systems, software and processes is also contemplated. For example, the results of one or more genetic analyses as described herein may be analysed using a computer system and processed by such a system utilising a computer-executable example of the analyses described herein.

Both the SNPs and the results of an analysis of the SNPs utilised in the present invention may be "provided" in a variety of mediums to facilitate use thereof. As used in this section, "provided" refers to a manufacture, other than an isolated nucleic acid molecule, that contains SNP information of the present invention. Such a manufacture provides the SNP information in a form that allows a skilled artisan to examine the manufacture using means not directly applicable to examining the SNPs or a subset thereof as they exist in nature or in purified form. The SNP information that may be provided in such a form includes any of the SNP information provided by the present invention such as, for example, polymorphic nucleic acid and/or amino acid sequence information, information about observed SNP alleles, alternative codons, populations, allele frequencies, SNP types, and/or affected proteins, identification as a responsive SNP or a resistance SNP, weightings (for example for use in an combined analysis as described herein), or any other information provided by the present invention.

In one application of this embodiment, the SNPs and the results of an analysis of the SNPs utilised in the present invention can be recorded on a computer readable medium. As used herein, "computer readable medium" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable media can be used to create a manufacture comprising computer readable medium having recorded thereon SNP information of the present invention. One such medium is provided with the present application, namely, the present application contains computer readable medium (floppy disc) that has nucleic acid sequences used in analysing the SNPs utilised in the present invention provided/recorded thereon in ASCII text format in a Sequence Listing along with accompanying Tables that contain detailed SNP and sequence information.

As used herein, "recorded" refers to a process for storing information on computer readable medium. A skilled artisan can readily adopt any of the presently known methods for recording information on computer readable medium to generate manufactures comprising the SNP information of the present invention.

A variety of data storage structures are available to a skilled artisan for creating a computer readable medium having recorded thereon SNP information of the present invention. The choice of the data storage structure will generally be based on the means chosen to access the stored information. In addition, a variety of data processor programs and formats can be used to store the SNP information of the present invention on computer readable medium. For example, sequence information can be represented in a word processing text file, formatted in commercially-available software such as WordPerfect and Microsoft Word, represented in the form of an ASCII file, or stored in a database application, such as OB2, Sybase, Oracle, or the like. A skilled artisan can readily adapt any number of data processor structuring formats (e.g., text file or database) in order to obtain computer readable medium having recorded thereon the SNP information of the present invention.

By providing the SNPs and/or the results of an analysis of the SNPs utilised in the present invention in computer readable form, a skilled artisan can routinely access the SNP information for a variety of purposes. Computer software is publicly available which allows a skilled artisan to access sequence information provided in a computer readable medium. Examples of publicly available computer software include BLAST (Altschul et at, J. Mol. Biol. 215:403-410 (1990)) and BLAZE (Brutlag et at, Comp. Chem. 17:203-207 (1993)) search algorithms.

The present invention further provides systems, particularly computer-based systems, which contain the SNP information described herein. Such systems may be designed to store and/or analyze information on, for example, a number of SNP positions, or information on SNP genotypes from a number of individuals. The SNP information of the present invention represents a valuable information source. The SNP information of the present invention stored/analyzed in a computer-based system may be used for such applications as predicting a subject's likely responsiveness to an antiplatelet agent, in addition to computer-intensive applications as determining or analyzing SNP allele frequencies in a population, mapping disease genes, genotype-phenotype association studies, grouping SNPs into haplotypes, correlating SNP haplotypes with response to particular drugs, or for various other bioinformatic, pharmacogenomic, drug development, or human identification/forensic applications.

As used herein, "a computer-based system" refers to the hardware, software, and data storage used to analyze the SNP information of the present invention. The minimum hardware of the computer-based systems of the present invention typically comprises a central processing unit (CPU), an input, an output, and data storage. A skilled artisan can readily appreciate that any one of the currently available computer-based systems are suitable for use in the present invention. Such a system can be changed into a system of the present invention by utilizing the SNP information, such as that provided herewith on the floppy disc, or a subset thereof, without any experimentation.

As stated above, the computer-based systems of the present invention comprise data storage having stored therein SNP information, such as SNPs and/or the results of an analysis of the SNPs utilised in the present invention, and the necessary hardware and software for supporting and implementing one or more programs or algorithms. As used herein, "data storage" refers to memory which can store SNP information of the present invention, or a memory access facility which can access manufactures having recorded thereon the SNP information of the present invention.

The one or more programs or algorithms are implemented on the computer-based system to identify or analyze the SNP information stored within the data storage. For example, such programs or algorithms can be used to determine which nucleotide is present at a particular SNP position in a target sequence, to analyse the results of a genetic analysis of the SNPs described herein, or to derive a SNP score as described herein. As used herein, a "target sequence" can be any DNA sequence containing the SNP position(s) to be analysed, searched or queried.

A variety of structural formats for the input and output can be used to input and output the information in the computer-based systems of the present invention. An exemplary format for an output is a display that depicts the SNP information, such as the presence or absence of specified nucleotides (alleles) at particular SNP positions of interest. Such presentation can provide a rapid, binary scoring system for many SNPs or subjects simultaneously. It will be appreciated that such output may be accessed remotely, for example over a LAN or the internet. Typically, given the nature of SNP information, such remote accessing of such output or of the computer system itself is available only to verified users so that the security of the SNP information and/or the computer system is maintained. Methods to control access to computer systems and the data residing thereon are well-known in the art, and are amenable to the embodiments of the present invention.

One exemplary embodiment of a computer-based system comprising SNP information of the present invention that can be used to implement the present invention includes a processor connected to a bus. Also connected to the bus are a main memory (preferably implemented as random access memory, RAM) and a variety of secondary storage devices, such as a hard drive and a removable medium storage device. The removable medium storage device may represent, for example, a floppy disc drive, a CD-ROM drive, a magnetic tape drive, etc. A removable storage medium (such as a floppy disc, a compact disc, a magnetic tape, etc.) containing control logic and/or data recorded therein may be inserted into the removable medium storage device. The computer system includes appropriate software for reading the control logic and/or the data from the removable storage medium once inserted in the removable medium storage device. The SNP information of the present invention may be stored in a well-known manner in the main memory, any of the secondary storage devices, and/or a removable storage medium. Software for accessing and processing the SNP information (such as SNP scoring tools, search tools, comparing tools, etc.) preferably resides in main memory during execution.

Accordingly, the present invention provides the invention provides a system for determining a subject's response to an antiplatelet agent, said system comprising:

computer processor means for receiving, processing and communicating data;

storage means for storing data including a reference genetic database of the results of at least one genetic analysis with respect to response to an antiplatelet agent or with respect to a disease or condition associated with platelet aggregation, and optionally a reference non-genetic database of non-genetic risk factors for a disease or condition associated with platelet aggregation; and a computer program embedded within the computer processor which, once data consisting of or including the result of a genetic analysis for which data is included in the reference genetic database is received, processes said data in the context of said reference databases to determine, as an outcome, the subject's response to an antiplatelet agent, said outcome being communicable once known, preferably to a user having input said data.

The present invention further provides a computer program for use in a computer system as described, and the use of the results of such systems and programs in the prediction or determination of a subject's response to an antiplatelet agent, or in determining the suitability of a subject for a treatment regime or an intervention as described herein.

The predictive methods of the invention allow a number of therapeutic interventions and/or treatment regimens to be assessed for suitability and implemented for a given subject. The simplest of these can be the provision to the subject of motivation to implement a lifestyle change, for example, where the subject is a current smoker, the methods of the invention can provide motivation to quit smoking.

The manner of therapeutic intervention or treatment will be predicated by the nature of the polymorphism(s) and the biological effect of said polymorphism(s). For example, where a resistance polymorphism is associated with a change in the expression of a gene, intervention or treatment may be directed to the restoration of normal expression of said gene, by, for example, administration of an agent capable of modulating the expression of said gene. Where a polymorphism is associated with decreased expression of a gene, therapy can involve administration of an agent capable of increasing the expression of said gene, and conversely, where a polymorphism is associated with increased expression of a gene, therapy can involve administration of an agent capable of decreasing the expression of said gene. Methods useful for the modulation of gene expression are well known in the art. For example, in situations where a polymorphism is associated with upregulated expression of a gene, therapy utilising, for example, RNAi or antisense methodologies can be implemented to decrease the abundance of mRNA and so decrease the expression of said gene. Alternatively, therapy can involve methods directed to, for example, modulating the activity of the product of said gene, thereby compensating for the abnormal expression of said gene.

Where a resistance polymorphism is associated with decreased gene product function or decreased levels of expression of a gene product, therapeutic intervention or treatment can involve augmenting or replacing of said function, or supplementing the amount of gene product within the subject for example, by administration of said gene product or a functional analogue thereof. For example, where a polymorphism is associated with decreased enzyme function, therapy can involve administration of active enzyme or an enzyme analogue to the subject. Similarly, where a polymorphism is associated with increased gene product function, therapeutic intervention or treatment can involve reduction of said function, for example, by administration of an inhibitor of said gene product or an agent capable of decreasing the level of said gene product in the subject. For example, where a SNP allele or genotype is associated with increased enzyme function, therapy can involve administration of an enzyme inhibitor to the subject.

Likewise, when a responsive polymorphism is associated with upregulation of a particular gene or expression of an enzyme or other protein, therapies can be directed to mimic such upregulation or expression in an individual lacking the resistive genotype, and/or delivery of such enzyme or other protein to such individual Further, when a responsive polymorphism is associated with downregulation of a particular gene, or with diminished or eliminated expression of an enzyme or other protein, desirable therapies can be directed to mimicking such conditions in an individual that lacks the responsive genotype.

In preferred embodiments, the therapeutic intervention may be the substitution of one antiplatelet agent for another, such as the substitution of prasugrel for clopidogrel, or the modification of the dosage regime, such as increased or decreased dosage, including increased or decreased loading or maintenance dosages.

The relationship between the various polymorphisms identified above and the responsiveness of a subject to an anti-platelet agent, or susceptibility (or otherwise) of a subject to a disease or condition associated with platelet aggregation also has application in the design and/or screening of candidate therapeutics. This is particularly the case where the association between a resistance polymorphism is manifested by either an upregulation or downregulation of expression of a gene. In such instances, the effect of a candidate therapeutic on such upregulation or downregulation is readily detectable.

For example, in one embodiment existing human vascular organ and cell cultures are screened for SNP genotypes as set forth above. (For information on human vascular organ and cell cultures, see for example: Clare Wise ED., Epithelial Cell Culture Protocols, 2002, ISBN 0896038939, Humana Press Inc. NJ; Endothelial Cell Culture, Roy Bicknell, ED., 1996, ISBN 0521550246, Cambridge University Press, UK; Cell Culture Models of Biological Barriers, Claus-Michael Lehr, ED., 2002, ISBN 0415277248, Taylor and Francis, UK; each of which is hereby incorporated by reference in its entirety.) Cultures representing relevant genotype groups are selected, together with cultures which are putatively "normal" in terms of the expression of a gene which is either upregulated or downregulated where a polymorphism is present.

Samples of such cultures are exposed to a library of candidate therapeutic compounds and screened for: (a) downregulation of genes that are normally upregulated in resistance genotypes; or (b) upregulation of genes that are normally downregulated in resistance genotypes. Compounds are selected for their ability to alter the regulation and/or action of genes in a culture having a resistance genotype.

Similarly, where the polymorphism is one which when present results in a physiologically active concentration of an expressed gene product outside of the normal range for a subject (adjusted for age and sex), and where there is an available prophylactic or therapeutic approach to restoring levels of that expressed gene product to within the normal range, individual subjects can be screened to determine the likelihood of their benefiting from that restorative approach. Such screening involves detecting the presence or absence of the polymorphism in the subject by any of the methods described herein, with those subjects in which the polymorphism is present being identified as individuals likely to benefit from treatment.

The invention will now be described in more detail, with reference to the following non-limiting examples.

Example 1

Pharmacogenomic Analysis of Clopidogrel Response

Introduction

This example describes a randomized, placebo controlled trial to compare the effect of a split-dose 1,200 mg clopidogrel loading dose with standard 600 mg clopidogrel and to measure pharmacogenomic analysis of genotypes suspected to influence the response to clopidogrel.

Methods

Patients

The study protocol was approved by the Northern Regional Ethics Committee of New Zealand. Eligible patients were defined as all-corners for elective percutaneous coronary intervention who were on aspirin and naëve to clopidogrel. Exclusion criteria were; a bleeding or platelet disorder, previous gastrointestinal bleeding or gastric ulcer/duodenal ulcer/gastritis within the last six months, sensitivity/allergy to aspirin/clopidogrel/verapamil, renal failure (creatinine clearance eGFR<30 mls/min), anaemia Hb<115 mg/dL, thrombocytopaenia and medication inhibiting CYP3A4. Patients on warfarin were included if the INR was <1.5 at study entry and warfarin was to be withheld for the duration of the clopidogrel course.

60 patients undergoing elective percutaneous coronary intervention enrolled in the randomised PRINC trial had platelet function measured using the VerifyNow P2Y12 analyzer. There was greater platelet inhibition with a split 1200 mg compared with a standard 600 mg clopidogrel loading dose, and with a 150 mg compared with a 75 mg daily maintenance dose.

Randomisation and Medication

Patients were randomised into equal groups using a computerised random number generator. Block randomisation was not used, explaining the unbalanced grouping to treatment allocations. Clopidogrel was broken in half and repackaged into gelatine capsules packed with lactose powder to match placebo. Investigators and subjects were blinded to treatment allocation. A target of 120 patients was predefined for completion of the study. Patients were randomised in a 2×2 factorial design 1:1 to receive either 5 mg intra-arterial verapamil or placebo at baseline, and 1:1 to receive either placebo or 600 mg clopidogrel, two hours from baseline (FIG. 1.) All subjects received 600 mg clopidogrel at the time of PCI, ten minutes after administration of verapamil. At discharge patients were randomized to receive either 75 mg or 150 mg once daily for one week and regular 75 mg once daily dosing thereafter. Adherence to the treatment regimen was tested by a phone interview and pill count.

Study Design

2×2 factorial, randomized, placebo-controlled, double-blind study.

Blood Sampling

Arterial blood was sampled through 6Fr femoral sheaths and transferred immediately to 3.2% citrate 2 ml vacutainer tubes (Cat. #454321 Greiner Vacuette®, Greiner, Kremsmuenster, Austria), using a 20 G needle and syringe. After sheath removal blood was drawn by venepucture directly into vacutainer tubes. After collection the tubes were inverted four times for adequate mixing of the anticoagulant and left for ten minutes at 24 degrees before testing. Platelet function was tested at baseline, two, four and seven hours from first clopidogrel loading and at seven days.

Platelet Function Analysis

Platelet function was measured using the point-of-care device, the VerifyNow rapid platelet function analyser (RPFA) and its corresponding P2Y12 cartridge (Accumetrics Ltd, San Diego, Calif., U.S.A). This device uses fibrinogen coated microbeads, an agonist of adenosine diphosphate (ADP) and light transmittance through whole blood, to measure platelet agglutination. The output of the device is measured as the proprietary platelet response unit (PRU). The P2Y12 cartridge result correlates favourably with light transmittance aggregometry, (van Werkum et al.) with reported increased sensitivity to the P2Y12 receptor due to the addition of prostaglandin E2 to the reaction chamber (Serebruany V L et al (2005)). Percent inhibition is reported as the percentage change from baseline using a BASE unit. This BASE unit is derived from a second channel run parallel with the ADP channel using the agonist iso-TRAP (Thrombin Receptor Activating Peptide). From this point "percentage inhibition" will reflect this formula: % Inhibition=[(BASE−PRU)×100]/BASE.

Clopidogrel Nonresponsiveness

It has been proposed that "resistance" is best defined as residual post treatment activity in the target pathway of an antiplatelet agent.[1] Non-responsiveness to clopidogrel was defined as <10% maximal inhibition at seven hours and by a <10% change in inhibition from baseline using the absolute PRU values (Lau W C et al. (2004) and Lev E I et al (2006)).

Endpoints

Primary endpoints were RPFA values at two, four, seven hours and seven days, with the seven hour value being considered the maximum peak effect.

Secondary endpoints were plasma parent drug levels at four hours, troponin and creatinine kinase at seven hours and safety outcomes including femoral haematoma, pseudoaneurysm, other bleeding events and adverse drug reactions. Further post-hoc analysis was performed to determine predictability of drug response. A receiver operator characteristic (ROC) analysis was conducted to investigate whether platelet inhibition at two hours predicted Clopidogrel non-responsiveness at seven hours and seven days.

Pharmacogenetic Analysis

DNA was extracted from whole blood using the QIAamp® DNA Blood Mini Kit (Cat. #51104. QIAGEN N.V., Netherlands) and stored at −20 degrees C. DNA yield and quality was assessed using the Nanodrop® ND-1000 spectrophotometer (NanoDrop Technologies, Wilmington, Del., U.S.A). Genotyping for the ABCB1*2 haplotype (ABCB1 SNPs 1236C>T, 2677G>T>A and 3435C>T); CYP3A4*1B, *3, *4; CYP3A5*2*3>>*4, CYP2C9*1, *2, *3 and CYP2C19*2*3*17 was performed using validated Taqman® assays (Applied Biosystems, Foster City, Calif. 94404, U.S.A.). Genotyping for the P2Y12 H2 haplotype, Pregnane X receptor 4760G>A, 252A>G, 275A>G and Carboxylesterase intronic SNP (IVS10-88) were performed using iPlex® assays on the Sequenom® Autoflex Mass spectrometer and the Samsung 24 pin nanodispensor (John Hopkins Court, San Diego, Calif., U.S.A). Genotyping using the Sequenom® Mass spectrometer was performed at the Australian Genome Research Facility (University of Queensland, St Lucia QLD 4072, Australia). The call rate for this method was 96.4% whereas for Taqman® it was 100%. The ABCB1 3435C>T SNP was tested by both methods and there was 100% concordance between results. The relevant reference sequence numbers and functional effects of the SNPs are outlined in Table 2.

The principal time point of interest for comparisons of genotype to drug response was specified as two hours after the first loading dose as at this point all patients had received only 600 mg. This time interval was also deemed the most significant in terms of assessing clopidogrel efficacy as the growth rate in pharmcodynamic effect is greatest in this period and likely to be strongly influenced by rate limiting steps. The effect of different dosages on response in genotype groups was assessed at four hours.

Statistical Analysis

Power

The numbers required to reach statistical power were calculated using figures for platelet inhibition effected by higher doses of clopidogrel. A receiver operator characteristic was used to assess the predictive value of the percentage platelet inhibition at two hours compared to seven hours. The Wilcoxon rank sum test was used for nonparametric data and the Kruskal Wallis test was used when more than three groups were being analysed. ANOVA was used to assess the differences between genotype groups within a single gene and ANCOVA was used to assess the influence of pharmacogenetics versus drug dose on the variance in platelet inhibition. Statistical adjustment for multiple hypothesis testing was not used. The software used for the analysis was SAS institute (version 9.1) and R (version 2.1.1).

Results

Platelet Inhibition

Platelet inhibition at four hours differed significantly between the 600 mg loading dose and the 1,200 mg split loading dose (23.7% versus 42%, P=0.03). This difference was sustained at seven hours (28.7% versus 48.9%, P=0.03) but was not seen at seven days (35.7% versus 44.5%, P=0.43). At one week a significant difference in platelet inhibition was seen between the group receiving 75 mg of clopidogrel compared to 150 mg once daily (28.8% versus 49.8%, P=0.01).

Prediction of Response with Phenotyping

A receiver operator characteristic analysis was conducted to investigate the whether early testing at two hours predicted response to clopidogrel at later time intervals. Platelet inhibition at two hours significantly predicted clopidogrel resistance at seven hours (p=0.02). There were fewer non-responders in the 1,200 mg group than the 600 mg group; two out of 37 in the high dose group (5%) vs. six out of 26 in the low dose group (26%) had seven hour percent inhibition <10%. The AUC for these ROC curves was 0.90. Platelet inhibition of less than two percent, at two hours, was most effective at predicting non-response (inhibition <10 percent) in all patients, regardless of dose, at seven hours (Sensitivity 100%, and specificity 88%) (FIG. 1).

Prediction of Response with Genotyping

The frequency of the tested genotypes with reported population frequencies is outlined in Table 3.

CYP2C19 Polymorphisms

Figure 2:
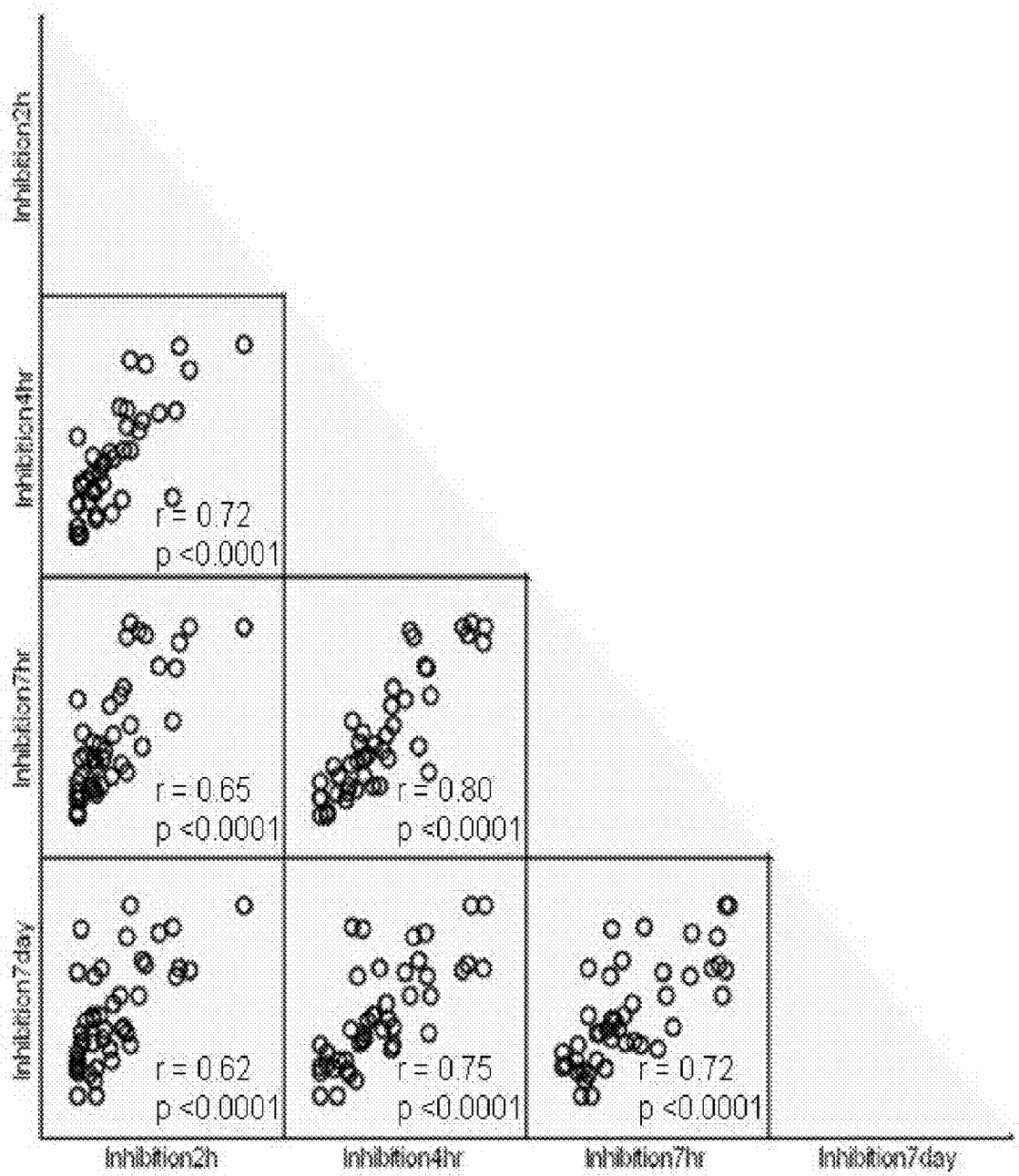
FIG. 2 shows a Pearson correlation matrix showing relationship between platelet function response at two time intervals, and the predictability of late Inhibition of Platelet Activity based on earlier time intervals after clopidogrel dosing. Platelet inhibition of less than two percent, at two hours, predicted non-response at seven hours (inhibition <10 percent), with a sensitivity of 100%, and specificity of 88%.

CYP2C19*2, *4 (loss of function carriers) and *17 (ultra-metabolisers) carriers had reduced platelet inhibition 2 hours after a 600 mg dose (13+/−20%), compared with CYP2C19*1*1 (normal function) carriers (26+/−20%, p=0.02) (FIG. 2). CYP2C19*1*1 carriers had similar platelet inhibition after a 1200 and 600 mg loading dose at four hours (51+/−28% and 35+/−27% p=0.2) (FIG. 3) and after a 150 and 75 mg daily maintenance dose (51+/−25% and 40+/−18%, p=0.3) (FIG. 5). In contrast, CYP2C19*2 or *4 carriers had increased platelet inhibition with the higher loading (36+/−24% and 16+/−13%, p=0.008) (FIG. 4), and maintenance dose regimens (49+/−31% and 24+/−18%, p=0.02) (FIG. 6).

CYP2C19*17 homozygotes occurred in higher frequency in the study group than would be expected in the general population. There were 16 (27%) CYP2C19*17 (T allele)

heterozygotes and 4 (7%)*17 homozygotes. These subjects identified themselves as of European descent. The frequency of these genotypes in the Hapmap database (CEU) is 0.4 and 0.02 respectively.

CYP2C9 Polymorphisms

CYP2C9*1*1 carriers had a reduced early response to clopidogrel compared to *1*2 carriers (P=0.04 for 2 hr inhibition, comparison by ANOVA). However, this trend did not remain consistent throughout the time intervals. Platelet inhibition was also reduced at 4 and 7 hrs in *1*3 carriers in the 600 mg group (p=0.06).

Combined Effects of 2C19 and 2C9 Polymorphisms

All individuals were aggregated based on their CYP2C19 and 2C9 genotype status as either responders (CYP2C19*1*1, CYP2C9*1 or CYPC19*2 carriers) or poor responders (2C19*2, CYPC19*4, CYPC19*17, or CYPC192C9*3). Despite the different dosing regimens of clopidogrel, platelet inhibition at seven hours was significantly influenced by poor responder genotype (p=0.03, Wilcoxon, see FIG. 7). Two individuals carried both 2C19 and 2C9 poor responder genotypes. Platelet inhibition at seven hours was 8% and 11% in these individuals. ANCOVA was used to compare the influence of genetics to clopidogrel dosing on platelet inhibition at 7 hours. The F value was 7.19 for dosing (p=0.0096) and 6.54 for genetics (p=0.013), suggesting that the influence of pharmacogenomics on the observed variance in maximal platelet inhibition was comparable to that of clopidogrel dose.

CYP3A5 Polymorphisms

*1*1 functional homozygotes had a reduced response to clopidogrel at all time intervals, however there were insufficient numbers in this group for a determination of the statistical significance of this observation.

P-Glycoprotein (ABCB1) Polymorphisms

The ABCB1*2 haplotype was infrequent (n=6) and showed a trend towards reduced inhibition at two hours however this was not statistically significant and this haplotype did not appear to influence the pharmacodynamic response to clopidogrel at any other time interval.

P2Y12 H2 Haplotype

Homozygotes with the P2Y12 H2 haplotype denoted by the insertion SNP i-T744C were rare in the cohort. Two subjects were CC homozygotes. These individuals did not display higher than average baseline platelet aggregation, denoted by a high PRU value, however the platelet inhibition at two hours after 600 mg clopidogrel was <2% for both individuals.

NR1I2 (hPXR)

The Pregnane X receptor SNPS 252A>G, 275A>G appeared to be in complete LD as has been previously described. 4760G>A was closely linked, but not in 7 individuals. Carriers of the G allele had lower platelet inhibition at 2 hrs (p<0.01, Kruskal Wallis). This trend remained consistent at later time intervals and in maintenance dosing.

Cumulative Effect of Genotypes

Four genotypes that influenced the response to clopidogrel were scored 0 for absence and +1 for presence. The effect of two of these genotypes on the antiplatelet effect of clopidogrel, when tested in isolation, did not reach statistical significance. However, when aggregated there was a clear dose response relationship between the presence of none, one, two, three or four of the below genotypes and response to clopidogrel at two hours (FIG. 8):

the 1A/G (rs28399504) GG or GA genotype in the gene encoding CYP2C19 (also referred to herein as a CYP2C19*4 genotype or CYP2C19*4 carrier); or the 19154G/A (rs4244285) AA or GA genotype in the gene encoding CYP2C19 (also referred to herein as a CYP2C19*2 genotype or CYP2C19*2 carrier);

the 42614A/C (rs1057910) CC or CA genotype in the gene encoding CYP2C9 (also referred to herein as a CYP2C9*3 genotype or CYP2C9*3 carrier);

the 275A/G (rs1464602) GG or GA genotype in the gene encoding NR1I2.

Discussion

The results presented above show that a split loading dose of 1,200 mg and a maintenance dose of 150 mg have a greater antiplatelet effect than standard dosing regimens. Furthermore, these results show that the loss of function CYP2C19*4 genotype and the ultra-metaboliser CYP2C19*17 genotype, in addition to the CYP2C19*2 genotype, are important in influencing the response to clopidogrel. Carriers of any of these genotypes display a reduced early response to clopidogrel after loading and sustained response after one week of maintenance therapy.

CYP2C19 has been reported to be important in the first step of biotransformation of the parent drug into the active metabolite, and a loss of function in this enzyme system reportedly leads to a reduction in the plasma levels of the active metabolite (Brant J T et al.). As shown here, CYP2C19*17 ultra-metabolisers also have a reduced pharmacodynamic response to the drug, suggesting that the active metabolite may also be a substrate for CYP2C19.

Of considerable importance is the finding that an increased dose of 1,200 mg split over two hours may achieve greater platelet inhibition in *2 and *4 carriers compared with the functional *1 wildtype carriers. This is supported by the results observed in the higher maintenance dose group. This is contrary to the recent observations in a study by Fontana et al. Notably, that study looked at the effects of a dose-genotype interaction only in those deemed poor responders based on VASP platelet function testing (Fontana P, Senouf D et al (2007)).

Four publications have reported that CYP2C19 is important in the metabolism of clopidogrel (Brandt, Close S L et al. (2007), Hulot J S et al. (2006), Fontana P, Senouf D et al. (2007), and Fontana P, Hulot J S et al (2007). The first reported that CYP2C19*2 heterozygotes had no significant change in platelet function after seven days of 75 mg daily of clopidogrel. In this study, platelet function was measured using both 10 μmol/L ADP light transmittance aggregometry and vasodilator stimulated phosphorylation (VASP) (Hulot J S et al. (2006)). The second study replicated this finding in a cohort of normal subjects given a loading dose of 300 mg and maintenance dosing of 75 mg clopidogel for one week. Platelet inhibition, measured by 20 μmol/L ADP aggregometry at seven days after loading, was reported to be significantly less in the subjects carrying the CYP2C19*2 allele (Fontana P, Hulot J S et al. (2007)). The third study from the Eli Lilly laboratories reported that not only is the CYP2C19*2 allele influential in the response to clopidogrel but also CYP2C9*11 (*2/*2, *2/*3). CYP2C9 and 2C19 variants are not in linkage disequilibrium, but when considered together they reportedly account for 66.7% of poor-responders, defined as less than 20% inhibition of platelet activity to 20 μmol/L ADP aggregometry.

The above results support a pharmacogenomic approach to antiplatelet (and particularly clopidogel) therapy. For example, the 2C19*2 loss-of-function genotypes are common and present in the general population in frequencies of 12.7% of Caucasians, 18.2% of African Americans and 28.9% of East Asians (Luo H R et al. (2006)). This variance has immediate implications for individualised treatment based on race and brings into question the application of large studies based on a single race e.g. the COMMIT/CCS-2 (Chen Z M et al. (2005)). For example, COMMIT/CCS-2 may have underestimated the efficacy of clopidogrel in the context of STEMI or conversely underestimated the bleeding risk. Also, drugs that are competitively metabolised or inhibit the activity of CYP2C19 have the potential to reduce the activity of clopidogrel. These include omeprazole, phenyloin and SSRIs such as fluoxetine. Omeprazole has been reported to negatively interact with clopidogrel (Fontana P, Senouf D et al. (2007); Gilard M, Arnaud B, Le Gal G et al. (2006)). 20 subjects in the present study were on omeprazole, but no influence on platelet function was found in any of the patient groups.

This study indicates that an individualised treatment regimen, targeting carriers of these genotypes, may provide a greater pharmacodynamic response in poorly responsive subjects than in wildtype carriers.

One such regimen may take into account a consideration of the benefit of prasugrel over clopidogrel. Prasugrel reportedly has improved pharmacokinetics. It is rapidly hydrolysed by esterases and then metabolised into its active metabolite by CYP pathways that are not as dependent on CYP2C19 and 2C9 as clopidogrel. This may account for the reduced inter-individual variability and lower frequency of non-responders reported in subjects taking this drug (Brandt J T, Close S L et al. (2007)). It will be appreciated, however, that despite prasugrel's more desirable pharmacokinetics using this drug may not be appropriate in all individuals. Personalised therapy targeting those who carry the poorly responsive gene variants (CYP2C19 or 2C9 variants) may be more efficacious and cost effective than a "one-dose-fits all" philosophy.

TABLE 2

Candidate SNPs Associated With Clopidogrel Response

| Allele | SNP | Reference Sequence No. | Functional Effect | Effect on Clopidogrel | Reference |
|---|---|---|---|---|---|
| ABCB1*2 | 1236C > T | rs1128503 | Increased intestinal efflux of drugs | — | Herein |
|  | 3435C > T | rs1045642 |  | negative | Taubert et al[9] |
|  | 2677G > T > A | rs2032582 |  | — | — |
| CYP3A4*1B | −392A > G | rs2740574 | Reduced enzyme function | none | Angiolillo et al (2006) |
| CYP3A4*3 | 23171T > C | rs4986910 | Reduced enzyme function | none | Angiolillo et al (2006) |
| CYP3A4*4 | 13871A > G | ? | Reduced enzyme function | — | — |
| CYP3A5*1 | 6986G > A | rs776746 | Normal enzyme function | positive | Suh (2006) |
|  | 31611T > C |  |  |  |  |
| CYP3A5*3 | 6986A > G |  | Non-functional enzyme | negative | Suh (2006) |
| CYP2C19*1 | — | — | Normal enzyme function | normal | Romkes et al (1991) Fontana, Hulot et al (2007) Hulot et al (2006) Brandt, Close SL et al (2007) |
| CYP2C19*2 | 19154G > A | rs4244285 | Reduced enzyme function | negative | Fontana, Hulot et al (2007) Hulot et al (2006) Brandt, Close SL et al (2007) |
| CYP2C19*4 | 1A > G | rs28399504 | Reduced enzyme function | — | Herein |
| CYP2C19*17 | −806C > T | rs12248560 | Increased enzyme function | — | Herein |
| CYP2C9*1 | — | — | Normal enzyme function | normal | Brandt, Close SL et al (2007) |
| CYP2C9*2 | 3608C > T | rs1799853 | Reduced enzyme function | negative | Brandt, Close SL et al (2007) |
| CYP2C9*3 | 42614A > C | rs1057910 | Reduced enzyme function | negative | Brandt, Close SL et al (2007) |
| P2Y12 H2 Haplotype | i-T744C | rs2046934 | Increased platelet response to ADP | none | Von Beckerath et al (2005) |
| hPXR | g.4760G > A | rs3732357 | Increased midazolam clearance | — | Herein |
|  | 275A > G | rs1464602 | Reduced midazolam clearance | — | Herein |

ABCB1 = P-glycoprotein gene,
CYP = Cytochrome P450,
hPXR = Human Pregnane X Receptor,
CES = Carboxylesterase.
Dash denotes information not available.
*1normal variants are denoted by the absence of variant SNPs

TABLE 3

Frequency of Detectable Alleles Compared to Hapmap Database

| Allele | SNP | Reference Sequence No. | Frequency (HapMap) homozygotes | heterozygotes |
|---|---|---|---|---|
| ABCB1*2 | 1236C > T | rs1128503 | 0.13 | 0.62 |
|  | 3435C > T | rs1045642 | 0.22 (0.24) | 0.63 (0.60) |
|  | 2677G > T > A | rs2032582 | 0.12 (0.11) | 0.6 (0.56) |
| CYP3A5*1 | — | — | 0.05 | 0.05 |
| CYP3A5*3 | 6986A > G | — | 0.92 | 0.05 |
| CYP2C19*1 | 80161A > G | rs3758581 | 0.4 (0.90)? | 0.48 (0.10)? |
| CYP2C19*2 | 19154G > A | rs4244285 | 0 (0.05) | 0.27 (0.2) |
| CYP2C19*4 | 1A > G | rs28399504 | 0 | 0.05 |
| CYP2C19*17 | −806C > T | rs12248560 | 0.07 (0.02) | 0.27 (0.4) |
| CYP2C9*1 | 1188T > C | — | 0.65 | 0.33 |
| CYP2C9*2 | 3608C > T | rs1799853 | 0.02 (0) | 0.25 (0.21) |
| CYP2C9*3 | 42614A > C | rs1057910 | 0 (0) | 0.05 (0.12) |
| P2Y12 H2 Haplotype | i-T744C | rs2046934 | 0.03 (0.03) | 0.25 (0.38) |

INDUSTRIAL APPLICATION

The present invention is directed to methods for predicting or determining a subject's response to an antiplatelet agent, and to methods for determining a subject's suitability to a treatment regime or intervention. The methods comprise the analysis of polymorphisms herein shown to be associated with responsiveness to an antiplatelet agent, or the analysis of results obtained from such an analysis. The use of polymorphisms herein shown to be associated with responsiveness to an antiplatelet agent in the assessment of a subject's suitability to a treatment regime or intervention are also provided, as are nucleotide probes and primers, kits, and microarrays suitable for such assessment. Methods of treating subjects having the polymorphisms herein described are also provided. Methods for screening for compounds able to modulate the expression of genes associated with the polymorphisms herein described are also provided.

All patents, publications, scientific articles, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods described herein are representative of various embodiments or preferred embodiments and are exemplary only and not intended as limitations on the scope of the invention. Other objects, aspects, examples and embodiments will occur to those skilled in the art upon consideration of this specification, and are encompassed within the spirit of the invention as defined by the scope of the claims. It will be readily apparent to one skilled in the art that varying substitutions and modifications can be made to the invention disclosed herein without departing from the scope and spirit of the invention. The invention illustratively described herein suitably can be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification, thus indicating additional examples, having different scope, of various alternative embodiments of the invention. Also, the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of a Patent Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention.

CITATIONS

1. Lau W C, Gurbel P A, Watkins P B, et al. Contribution of hepatic cytochrome P450 3A4 metabolic activity to the phenomenon of clopidogrel resistance. *Circulation* 2004; 109(2):166-71.
2. Brandt J T, Close S L, Iturria S J, et al. Common polymorphisms of CYP2C19 and CYP2C9 affect the pharmacokinetic and pharmacodynamic response to clopidogrel but not prasugrel. *J Thromb Haemost* 2007.

3. Suh J W, Koo B K, Zhang S Y, et al. Increased risk of atherothrombotic events associated with cytochrome P450 3A5 polymorphism in patients taking clopidogrel. *Cmaj* 2006.
4. Hulot J S, Bura A, Villard E, et al. Cytochrome P450 2C19 loss-of-function polymorphism is a major determinant of clopidogrel responsiveness in healthy subjects. *Blood* 2006; 108(7):2244-7.
5. Fontana P, Senouf D, Mach F. Biological effect of increased maintenance dose of clopidogrel in cardiovascular outpatients and influence of the cytochrome P450 2C19*2 allele on clopidogrel responsiveness. *Thromb Res* 2007.
6. Angiolillo D J, Fernandez-Ortiz A, Bernardo E, et al. Contribution of gene sequence variations of the hepatic cytochrome P450 3A4 enzyme to variability in individual responsiveness to clopidogrel. *Arterioscler Thromb Vasc Biol* 2006; 26(8):1895-900.
7. Fontana P, Hulot J S, P DEM, Gaussem P. Influence of CYP2C19 and CYP3A4 gene polymorphisms on clopidogrel responsiveness in healthy subjects. *J Thromb Haemost* 2007; 5(10):2153-5.
8. von Beckerath N, Taubert D, Pogatsa-Murray G, Schomig E, Kastrati A, Schomig A. Absorption, metabolization, and antiplatelet effects of 300-, 600-, and 900-mg loading doses of clopidogrel: results of the ISAR-CHOICE (Intracoronary Stenting and Antithrombotic Regimen: Choose Between 3 High Oral Doses for Immediate Clopidogrel Effect) Trial. *Circulation* 2005; 112(19):2946-50.
9. Taubert D, von Beckerath N, Grimberg G, et al. Impact of P-glycoprotein on clopidogrel absorption. *Clin Pharmacol Ther* 2006; 80(5):486-501.
10. van Werkum J W, van der Stelt C A, Seesing T H, Hackeng C M, ten Berg J M. A head-to-head comparison between the VerifyNow P2Y12 assay and light transmittance aggregometry for monitoring the individual platelet response to clopidogrel in patients undergoing elective percutaneous coronary intervention. *J Thromb Haemost* 2006; 4(11): 2516-8.
11. Serebruany V L, Steinhubl S R, Berger P B, Malinin A I, Bhatt D L, Topol E J. Variability in platelet responsiveness to clopidogrel among 544 individuals. *J Am Coll Cardiol* 2005; 45(2):246-51.
12. Lev E I, Patel R T, Maresh K J, et al. Aspirin and clopidogrel drug response in patients undergoing percutaneous coronary intervention: the role of dual drug resistance. *J Am Coll Cardiol* 2006; 47(1):27-33.
13. Luo H R, Poland R E, Lin K M, Wan Y J. Genetic polymorphism of cytochrome P450 2C19 in Mexican Americans: a cross-ethnic comparative study. *Clin Pharmacol Ther* 2006; 80(1):33-40.
14. Chen Z M, Jiang L X, Chen Y P, et al. Addition of clopidogrel to aspirin in 45,852 patients with acute myocardial infarction: randomised placebo-controlled trial. *Lancet* 2005; 366(9497):1607-21.
15. Gilard M, Arnaud B, Le Gal G, Abgrall J F, Boschat J. Influence of omeprazol on the antiplatelet action of clopidogrel associated to aspirin. *J Thromb Haemost* 2006; 4(11):2508-9.
16. Romkes M, Faletto M, Blaisdell J, Raucy J, Goldstein J. Cloning and expression of complementary DNAs for multiple members of the human cytochrome P450IIC subfamily. *Biochemistry* 1991; 30:3247-3255.
17. Angiolillo, D J, Fernzndez-Ortiz, A, Bernardo, E, Ramirez, C, Barrera-Ramirez, C, Sabate, M Hernandez, R, Moreno, R, Escaned, J, Alfonso, F, Banuelos, C, Costa, M A, Bass, T A, Macaya, C. Identification of low responders to a 300-mg clopidogrel loading dose in patients undergoing coronary stenting. *Thromb Res* 2005; 115: 101-108.
18. Gurbel, P A, Bliden, K P, Hiatt, B L, O'Connor, C M. Clopidogrel for coronary stenting: response variability, drug resistance, and the effect of pretreatment platelet reactivity. *Circulation* 2003; 107:2908-2913.
19. Gurbel, P A, Tantry, U S. Drug insight: Clopidogrel nonresponsiveness. *Nat Clin Pract Cardiovasc Med* 2006; 3: 387-395.
20. Gurbel, P A, Bliden, K P, Hayes, K M, Yoho, J A, Herzog, W R, Tantry, U S. The relation of dosing to clopidogrel responsiveness and the incidence of high post-treatment platelet aggregation in patients undergoing coronary stenting. *J Am Cardio* 2005; 45: 1392-1396.
21. Mobley, J E, Bresee, S J, Wortham, D C, Craft, R M, Snider, CC, Carroll, R C. Frequency of nonresponse antiplatelet activity of clopidogrel during pretreatment for cardiac catheterization. *AM J Cardiol* 2004; 93: 456-458.
22. Muller, I, Besta, F, Schulz, C, Massberg, S, Schonig, A, Gawaz, M. Prevalence of clopidogrel non-responders among patients with stable angina pectoris scheduled for elective coronary stent placement. *Thromb Haemost* 2003; 89: 783-787.
23. Ajzenberg, N, Aubry, P, Huisse, M G, Cachier, A, E I, A W, Feldman, L J, Himbert, D, Baruch, D, Guillin, M C, Steg, P G. Enhanced shear-induced platelet aggregation in patients who experience subacute stent thrombosis: a case-control study. *J Am Coll Cardiol* 2005; 45: 1753-1756.
24. Barragan, P, Bouvier, J L, Roquebert, P O, Macaluso, G, Commeau, P, Comet, B, Lafont, A, Camoin, L, Walter, U, Eigenthaler, M. Resistance to thienopyridines: clinical detection of coronary stent thrombosis by monitoring of vasolidator-stimulated phosphoprotein phosphorylation. *Catheter Cardiovasc Interv* 2003; 59: 295-302.
25. Cuisset, T, Frere, C, Quilici, J, Barbou, F, Morange, P E, Hovasse, T, Bonnet, J L, Alessi, M C. High post-treatment platelet reactivity identified low-responders to dual antiplatelet therapy at increased risk of recurrent cardiovascular events after stenting for acute coronary syndrome. *J Thromb Haemost* 2006; 4: 542-549.
26. Gurbel, P A, Bliden, K P, Samara, W, Yoho, J A, Hayes, K, Fissha, M Z, Tantry, U S. Clopidogrel effect on platelet reactivity in patients with stent thrombosis: results of CREST study. *J Am Coll Cardiol* 2005; 46: 1827-1832.
27. Gurbel, P A, Bliden, K P, Guyer, K, Cho, P W, Zaman, K A, Kreutz, R P, Bassi, A K, Tantry, U S. Platelet reactivity in patients and recurrent events post-stenting: results of the PREPARE POST-STENTING Study. *J Am Coll Cardiol* 2005; 46: 1820-1826.
28. Matetzky, S, Shenkman, B, Guetta, V, Shechter, M, Bienart, R, Goldenberg, I, Novikov, I, Pres, H, Savion, N, Varon, D, Hod, H. Clopidogrel resistance is associated with increased risk of recurrent atherothrombotic events in patients with acute myocardial infarction. *Circulation* 2004; 109: 3171-3175.
29. Steinhubl, S R, Berger, P B, Mann, J T, III, Fry, E T, DeLago, A, Wilmer, C, Topol, E J. Early and sustained dual oral antiplatelet therapy following percutaneous coronary intervention: a randomized controlled trial. *JAMA* 2002; 288: 2411-2420.
30. Yusuf, S, Zhao, F, Mehta, S R, Chrolavicius, S, Tognoni, G, Fox, K K. Effects of clopidogrel in addition to aspirin in patients with acute coronary syndromes without ST-segment elevation. *N Engl J Med* 2001; 345: 494-502.
31. Braunwald, E, Antman, E M, Beasley, J W, Califf, R M, Cheitin, M D, Hochman, J S, Jones, R H, Kereiakes, D, Kupersmith, J, Levin, T N, Pepine, C J, Schaeffer, J W, Smith, E E, III, Steward, D E, Theroux, P, Gibbons, R J, Alpert, J S, Faxon, D P, Fuster, V, Gregoratos, G, et al. ACC/AHA 2002 guideline update for the management of 31. patients with unstable angina and non-ST-segment elevantion myocardial infarction—summary article: a report of the American College Cardiology/American Heart Association task force on practice guidelines (Committee on the Management of Patients with Unstable Angina). *J Am Coll Cardiol* 2002; 40: 1366-1374.
32. Smith, S C, Jr., Feldman, T E, Hirshfeld, J W, Jr., Jacobs, A K, Kern, M J, King, S B, III, Morrison, D A, O'Neil, W W, Schaff, H V, Whitlow, P L, Williams, D O, Antman, E M, Adams, C D, Anderson, J L, Faxon, D P, Fuster, V, Halperin, J L, Hiratzka, L F, Hunt, S A, Nishimura, R, et al. ACC/AHA/SCAI 2005 guideline update for percutaneous coronary intervention: a report of the American College of Cardiology/American Heart Association Task Force on Practice Guidelines (ACC/AHA/SCAI Writing Committee to Update 2001 Guidelines for Percutaneous Coronary Intervention). *Circulation* 2006; 113: e166-e286.
33. Asai, F, Jakubowski, J A, Naganuma, H, Brandt, J T, Matsushima, N, Hirota, T, Freestone, S, Winters, K J. Platelet inhibitory activity and pharmacokinetics of prasugrel (CS-747) a novel thienopyridine P2Y12 inhibitor: a single ascending dose study done in humans. *Platelets.* 2006; 17: 209-217.
34. Jakubowski, J A, Payne, C D, Brandt, J T, Weerakkody, G J, Farid, N A, Small, D S, Naganuma, H, Li, G Y, Winters, K J. The platelet inhibitory effects and pharmacokinetics of prasugrel after administration of loading and maintenance doses in healthy subjects. *J Cardiovasc Pharmacol* 2006; 47: 377-384.
35. Jernberg, T, Payne, C D, Winters, K J, Darstein, C, Brandt, J T, Jakubowski, J A, Naganuma, H, Siegbahn, A, Wallentin, L. Prasurgrel achieves greater inhibition aggregation and a lower rate of non-responders compared with clopidogrel in aspirin-treated patients with stable coronary artery disease. *Eur Heart J* 2006; 27: 1166-1173.
36. Matsushimi, N, Jakubowski, J A, Asai, F, Naganuma, H, Brandt, J T, Hirota, T, Freestone, S, Winters, K J. Platelet inhibitory activity and pharmacokinetics of prasugrel (CS-747) a novel thienopyridine P2Y12 inhibitor: a multiple-dose study in healthy humans. *Platelets.* 2006; 17:218-226.
37. Brandt, J T, Payne, C D, Wiviott, S D, Weerakkody, G, Farid, N A, Small, D S, Jakubowski, J A, Naganuma, H, Winters, K J. A comparison of prasugurel and clopidogrel loading doses on platelet function: magnitude of platelet inhibition is related to active metabolite formation. *Am Heart J* 2007; 153: 66.e9-66.e16.
38. Rehmel, J L, Eckstein, J A, Farid, N A, Heim, J B, Kasper, S C, Kurihara, A, Wrighton, S A, Ring, B J. Interactions of two major metabolites of prasugrel, a thienopyridine antiplatelet agent, with the cytocrhomes P450. *Drug Metab Dispos* 2006; 34: 600-607.
39. Gurbel P A, Bliden K P, DiChiara J, et al. Evaluation of dose-related effects of aspirin on platelet function: results from the Aspirin-Induced Platelet Effect (ASPECT) study. *Circulation* 2007; 115(25):3156-64.
40. Harrison P. Platelet function analysis. *Blood Rev* 2005; 19(2):111-23.
41. Eikelboom J W, Hirsh J, Weitz J I, Johnston M, Yi Q, Yusuf S. Aspirin-resistant thromboxane biosynthesis and the risk of myocardial infarction, stroke, or cardiovascular death in patients at high risk for cardiovascular events. *Circulation* 2002; 105(14):1650-5.
42. Geiger J, Brich J, Honig-Liedl P, et al. Specific impairment of human platelet P2Y(AC) ADP receptor-mediated signaling by the antiplatelet drug clopidogrel. *Arterioscler Thromb Vasc Biol* 1999; 19(8):2007-11.
43. Dyszkiewicz-Korpanty A M, Frenkel E P, Sarode R. Approach to the assessment of platelet function: comparison between optical-based platelet-rich plasma and impedance-based whole blood platelet aggregation methods. *Clin Appl Thromb Hemost* 2005; 11(1):25-35.
44. Schlammadinger A, Kerenyi A, Muszbek L, Boda Z. Comparison of the O'Brien filter test and the PFA-100 platelet analyzer in the laboratory diagnosis of von Willebrand's disease. *Thromb Haemost* 2000; 84(1):88-92.
45. Hayward C P, Harrison P, Cattaneo M, Ortel T L, Rao A K. Platelet function analyzer (PFA)-100 closure time in the evaluation of platelet disorders and platelet function: reply to a rebuttal. *J Thromb Haemost* 2006; 4(6):1432.
46. Coleman J L W J, Simon D I. Determination of individual response to aspirin therapy using the Accumetrics Ultegra RFPA-ASA system. *Point of Care.* 2004; 3(2):77-82.
47. Wheeler G L, Braden G A, Steinhubl S R, et al. The Ultegra rapid platelet-function assay: comparison to standard platelet function assays in patients undergoing percutaneous coronary intervention with abciximab therapy. *Am Heart J* 2002; 143(4):602-11.
48. Frelinger A L, 3rd, Furman M I, Linden M D, et al. Residual arachidonic acid-induced platelet activation via an adenosine diphosphate-dependent but cyclooxygenase-1- and cyclooxygenase-2-independent pathway: a 700-patient study of aspirin resistance. *Circulation* 2006; 113 (25):2888-96.
49. Savi, P, Herbert, J M. Clopidogrel and ticlopidine: P2Y12 adenosine diphosphate-receptor antagonists for the prevention of atherothrombosis. *Semin Throm Hemost* 2005; 31: 174-183.
50. Sugidachi, A, Asai, F, Ogawa, T, Inoue, T, Koike, H. The in vivo pharmaceutical profile of CS-747, a novel antiplatelet agent with platelet ADP receptor antagonist properties. *Br J Pharmacol* 2000; 129: 1439-1446.
51. Goto, S, Tamura, N, Ishida, H, Ruggeri, Z m. Dependence of platelet thrombus stability on sustained glycoprotein Iib/IIIa activation through adenosine 5' diphosphate receptor stimulation and cyclic calcium signaling. *J Am Coll Cardiol* 2006; 47: 155-162.
52. Cattaneo, M. The platelet P2Y receptors as targets for new antithrombotic drugs. *J Thromb Haemost* 2003; 1: 1133-1135.

The invention claimed is:

1. A method comprising:
   a) analyzing a sample from a subject with a SNP detection assay to determine that said subject is homozygous for the −806C/T polymorphism in the CYP2C19 gene (CYP2C19*17), thereby generating a homozygous CYP2C19*17 genetic analysis result;
   b) inputting said homozygous CYP2C19*17 genetic analysis result into a system, wherein said system comprises:
      i) a computer processor for receiving, processing, and communicating data,
      ii) a storage component for storing data which contains a reference genetic database of results of at least one genetic analysis of CYP2C19*17 homozygosity with respect to response to clopidogrel, and
      iii) a computer program, embedded within said computer processor, which is configured to process said homozygous CYP2C19*17 genetic analysis result in the context of said reference database to determine, as an outcome, that said subject is an ultrametabolizer of said clopidogrel;
   c) processing said homozygous CYP2C19*17 genetic analysis result with said computer program in the context of said reference database to determine, as an outcome, that said subject is an ultrametabolizer of said clopidogrel;
   d) communicating said outcome from said computer program; and
   e) administering to said subject decreased loading and/or maintenance dosages of said clopidogrel compared to CYP2C19 wild-type dosage levels.

2. The method of claim 1, further comprising the step of analyzing said sample with a SNP detection assay for the presence or absence of the 636 G>A polymorphism in said CYP2C19 gene (CYP2C19*3 polymorphism).

3. The method of claim 2, further comprising the step of analyzing said sample with a SNP detection assay for the presence or absence of the 19154G/A polymorphism in said CYP2C19 gene (CYP2C19*2 polymorphism).

* * * * *

SEQUENCE LISTING

```
<160> NUMBER OF SEQ ID NOS: 12

<210> SEQ ID NO 1
<211> LENGTH: 51
<212> TYPE: DNA
<213> ORGANISM: Homo sapiens
<220> FEATURE:
```

```
<221> NAME/KEY: misc_feature
<222> LOCATION: (26)..(26)
<223> OTHER INFORMATION: N is T or C (for the 6986G/A (rs776746)
      polymorphism in the gene encoding CYP3A5)

<400> SEQUENCE: 1
atgtggtcca aacagggaag agatantgaa agacaaaaga gctctttaaa g          51

<210> SEQ ID NO 2
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: N is A or G (for the 1A/G (rs28399504)
      polymorphism in the gene encoding CYP2C19)

<400> SEQUENCE: 2
gtcttaacaa gaggagaagg cttcantgga tccttttgtg gtccttgtgc t          51

<210> SEQ ID NO 3
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: N is C or T (for the -806C/T (rs12248560)
      polymorphism in the gene encoding CYP2C19)

<400> SEQUENCE: 3
aaatttgtgt cttctgttct caaagnatct ctgatgtaag agataatgcg c          51

<210> SEQ ID NO 4
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: N is A or G (for the 275A/G (rs1464602)
      polymorphism in the gene encoding NR1I2)

<400> SEQUENCE: 4
acgtctcagg gcctcagctt gacctntccc ccaggttcag agtgtgggct g          51

<210> SEQ ID NO 5
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: N is A or G (for the 19154G/A (rs4244285)
      polymorphism in the gene encoding CYP2C19)

<400> SEQUENCE: 5
ttcccactat cattgattat ttcccnggaa cccataacaa attacttaaa a          51

<210> SEQ ID NO 6
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: N is C or A (for the 42614A/C (rs1057910)
      polymorphism in the gene encoding CYP2C9)
```

-continued

```
<400> SEQUENCE: 6
tgtggtgcac gaggtccaga gatacnttga ccttctcccc accagcctgc c        51

<210> SEQ ID NO 7
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: N is A or G (for the 636G>A (rs4986893)
      polymorphism in the gene encoding CYP2C19)

<400> SEQUENCE: 7
acatcaggat tgtaagcacc ccctgnatcc aggtaaggcc aagtttttg c          51

<210> SEQ ID NO 8
<211> LENGTH: 31
<212> TYPE: DNA
<213> ORGANISM: Homo sapiens
<220> FEATURE:
<221> NAME/KEY: misc_feature
<222> LOCATION: (16)..(16)
<223> OTHER INFORMATION: N is G or T (for the 516G>T (rs3745274)
      polymorphism in the gene encoding CYP2B6)

<400> SEQUENCE: 8
caccttcctc ttccantcca ttaccgccaa c                              31

<210> SEQ ID NO 9
<211> LENGTH: 30
<212> TYPE: DNA
<213> ORGANISM: Artificial Sequence
<220> FEATURE:
<223> OTHER INFORMATION: Synthetic - upstream primer for rs4986893
      polymorphism in CYP2C19*3 gene

<400> SEQUENCE: 9
tgaaaacatc aggattgtaa gcaccccctg                                30

<210> SEQ ID NO 10
<211> LENGTH: 30
<212> TYPE: DNA
<213> ORGANISM: Artificial Sequence
<220> FEATURE:
<223> OTHER INFORMATION: Synthetic - downstream primer for rs4986893
      polymorphism in CYP2C19*3 gene

<400> SEQUENCE: 10
atccaggtaa ggccaagttt tttgcttcct                                30

<210> SEQ ID NO 11
<211> LENGTH: 30
<212> TYPE: DNA
<213> ORGANISM: Artificial Sequence
<220> FEATURE:
<223> OTHER INFORMATION: Synthetic - upstream primer for the rs3745274
      polymorphism in CYP2B6*9 gene

<400> SEQUENCE: 11
ggccctcatg gaccccacct tcctcttcca                                30

<210> SEQ ID NO 12
<211> LENGTH: 30
<212> TYPE: DNA
```

-continued

```
<213> ORGANISM: Artificial Sequence
<220> FEATURE:
<223> OTHER INFORMATION: Synthetic - downstream primer for the rs3745274
      polymorphism in CYP2B6*9 gene

<400> SEQUENCE: 12
tccattaccg ccaacatcat ctgctccatc                                          30
```